United States Patent
Czarnik

(10) Patent No.: US 9,713,330 B1
(45) Date of Patent: *Jul. 25, 2017

(54) DEUTERIUM-ENRICHED ALDEHYDES

(71) Applicant: Deuteria Agrochemicals, LLC, Eastsound, WA (US)

(72) Inventor: Anthony W Czarnik, Reno, NV (US)

(73) Assignee: DEUTERIA AGROCHEMICALS, LLC, Eastsound, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/926,331

(22) Filed: Oct. 29, 2015

Related U.S. Application Data

(63) Continuation-in-part of application No. 14/680,065, filed on Apr. 7, 2015, now Pat. No. 9,179,670, which
(Continued)

(51) Int. Cl.
| | |
|---|---|
| *A01N 35/02* | (2006.01) |
| *A01N 25/28* | (2006.01) |
| *A01D 91/00* | (2006.01) |

(52) U.S. Cl.
CPC ............. *A01N 35/02* (2013.01); *A01D 91/00* (2013.01); *A01N 25/28* (2013.01)

(58) Field of Classification Search
CPC ...................................... A01N 35/02
See application file for complete search history.

(56) References Cited

U.S. PATENT DOCUMENTS

| 4,632,829 A | 12/1986 | Hedin et al. |
| 5,149,820 A | 9/1992 | Borretzen et al. |

(Continued)

FOREIGN PATENT DOCUMENTS

WO 95/26325 A2 10/1995

OTHER PUBLICATIONS

Stelinski et al (Entomologia Experimentalis et Applicata (2010), 134(1), 69-77).*
(Continued)

*Primary Examiner* — Benjamin Packard
(74) *Attorney, Agent, or Firm* — Vance Intellectual Property, PC

(57) ABSTRACT

The present invention generally relates to deuterium-enriched aldehydes, compositions comprising deuterium-enriched aldehydes, and methods for slowing the rate of aldehyde autoxidation. In one aspect, the present invention provides a composition comprising a compound of structure 1:

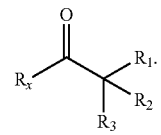

wherein: there are at least $6 \times 10^{18}$ molecules of the aldehyde and $R_x$ is hydrogen, wherein the deuterium isotope in $R_x$ is in an amount greater than 0.10 percent of the hydrogen atoms present in $R_x$.

22 Claims, 2 Drawing Sheets

Related U.S. Application Data is a continuation of application No. 14/214,912, filed on Mar. 15, 2014, now Pat. No. 9,023,336.

(60) Provisional application No. 61/817,006, filed on Apr. 29, 2013, provisional application No. 61/787,272, filed on Mar. 15, 2013.

(56) References Cited

U.S. PATENT DOCUMENTS

| | | |
|---|---|---|
| 6,001,346 A | 12/1999 | Delwiche et al. |
| 7,020,996 B2 | 4/2006 | Beroza et al. |
| 7,531,685 B2 | 5/2009 | Czarnik |
| 7,745,480 B2 | 6/2010 | Czarnik |
| 7,776,866 B2 | 8/2010 | Czarnik |
| 7,842,675 B2 | 11/2010 | Czarnik |
| 7,846,912 B2 | 12/2010 | Czarnik |
| 7,915,309 B2 | 3/2011 | Czarnik |
| 7,956,080 B2 | 6/2011 | Czarnik |
| 8,026,249 B2 | 9/2011 | Czarnik |
| 8,658,236 B2 | 2/2014 | Czarnik et al. |

OTHER PUBLICATIONS

Zhang, Jin-Ping, et al., An overlooked component: (Z)-9-tetradecenal as a sex pheromone in *Helicoverpa armigera*, J. Insect Physiology 2012, 58, 1209-16.
Sugie, Hajime, et al., A sex attractant of the cabbage webworm, *Hellula undalis Fabricius* (Lepidoptera: Pyralidae), Apl. Entomol. Zool. 2003, 38(1), 45-8.
Van Vorhis Key, S.E., et al., J. Chem. Ecology 1982, 8(7), 1057-63.
Bestmann, H. J., et al., Elektrophysiologische Messungen mit deuterierten Pheromonen zum Nachweis eines Isotopieeffektes, Naturwissenschaften 1989, 76, 422-4. (In German, no translation available.).
Prestwich, Glenn D., et al., Fluorinated Analogs of Aldehyde Components of Boll Weevil Pheromone: Synthesis and Biological Activity, J. Chem. Ecology 1988, 14(5), 1427-39.
Ding, Yu-Shin., et al., Chemical Studies of Proteins That Degrade Pheromones: Cyclopropanated, Fluorinated, and Electrophilic Analogs of Unsaturated Aldehyde Promoters, J. Chem. Ecology 1988, 14(11), 2033-46.
Prestwich, Glenn D., Fluorinated Sterols, Hormones and Pheromones: Enzyme-targeted Disruptants in Insects, Pestic. Sci. 1986, 37, 430-40.
Kushner, D.J.; Pharmacological Uses and Perspectives of Heavy Water and Deuterated Compounds; Canadian Journal of Physiology and Pharmacology 1999, 77(2), 79-88.
Buteau, Kristen C., Deuterated Drugs: Unexpectedly Nonobvious? J. High Tech. L. 2009, 10, 22-73.
Kim, J. et al., Deuterated analogues of 4,8-dimethyldecanal, the aggregation pheromone of Tirbolium castaneum: synthesis and pheromonal activity, J. Label Compd Radiopharm 2004, 47, 921-34.
Wang, H-L., et al., Biosynthesis of Unusual Moth Pheromone Components Involves Two Different Pathways in the Navel Orangeworm, *Amyelois transitella*, J. Chem. Ecol. 2010, 36, 535-47.
PCT/US14/30065 Written Opinion mailed Jul. 28, 2014 (corresponding PCT application).
PCT/US14/30065 International Search Report mailed Jul. 28, 2014 (corresponding PCT application).
Franco, Maria Isabel et al., Molecular vibration-sensing component in *Drosophila melanogaster* olfaction, PNAS 2011, 108(9), 3797-3802.
Hill, Shauna et. al., Small amounts of isotope-reinforced polyunsaturated fatty acids suppress lipid autoxidation, Free Radical Biology and Medicine,2012, 53, 893-906.
Witzgall, Peter, Pheromones-future techniques for insect control? Pheromones for Insect Control in Orchards and Vineyards, IOBC wprs Bulletin vol. 24(2), 2001, 114-22.
Dickens, J. C. et al., Green leaf volatiles interrupt aggregation pheromone response in bark beetles infesting southern pines, Experimentia 1992, 48, 523-4.
Nishizawa, M. et al., Asymmetric Synthesis of Chiral Geraniol-1-d and Related Terpenic Alocohols, Tetrahedron Letters, vol. 21, Jan. 1, 1980, p. 2821-2824.
Seebach, D. et al., Synthesis of 1-deuterioaldehydes. Benzaldehyde-1-d, Journal of Organic Chemistry, vol. 31, No. 12, Dec. 1, 1966, p. 4303-4304.
Degani, L. et al., 2-Deuterio-1,3-benzodithiolium perchlorates: A useful synthon for the preparation of aldehydes-1-d, Tetrahedron letters, vol. 22, No. 19, Jan. 1, 1981, p. 1821-1822.
Meyers, A. et al., Aldehydes from Dihydro-1,3-oxazines. I. A New Synthesis of Aliphatic Aldehydes and Their C-1 Deuterated Derivatives, Journal of the American Society, vol. 91, No. 3, Jan. 29, 1969, p. 763-764.
Kuwahara, Y. et al., Chemical Ecology on Astigmatid Mites XXXI. Geranial as the alarm pheromone of Histiostoma aboratorium Hughes (Astigmata: Histiostomidae), Appl. Ent. Zool, vol. 26, No. 4, Jan. 1, 1991.
Decou D., et al., Testing Wright's theory of olfaction with selectively deuterated (E)-2- hexen -1-al compounds, Developments in Food Science, Elsevier, vol. 37 A, Jan. 1, 1995, p. 525-548.
Marteau, C. et al., Oxidative degradation of fragrant aldehydes. Autoxidation by molecular oxygen, Tetrahedron, vol. 69, No. 10, Jan. 18, 2013, p. 2268-2275.
EP Application No. 14764255.7 (from PCT/US2014030065) Extended European Search Report, mailed Oct. 5, 2016.
CN Patent Application No. 2014800196528 (from PCT/US2014030065) Office Action, mailed Aug. 23, 2016.
CN Patent Application No. 2014800196528 (from PCT/US2014030065) Office Action Reporting Letter from CN agent, mailed Sep. 1, 2016.

\* cited by examiner

DEUTERIUM-ENRICHED ALDEHYDES

FIELD OF THE INVENTION

The present invention generally relates to deuterium-enriched aldehydes, compositions comprising deuterium-enriched aldehydes, and methods for slowing the rate of aldehyde autoxidation.

BACKGROUND OF THE INVENTION

Aldehydes are organic compounds containing a H—C(O)— moiety. They are used extensively in industrial processes. Formaldehyde, for instance, is produced on a scale of about 6,000,000 tons/year. Aldehydes are mainly used in the production of resins, but they also find application as precursors to plasticizers and other compounds used in the manufacturing of polymers. On a smaller scale, some aldehydes are used as ingredients in perfumes, flavors and compositions that modulate the behavior of insects, e.g., pheromone containing compositions.

Aldehydes have a tendency to react with atmospheric oxygen to form carboxylic acids (H—C(O)— oxidizes to $HO_2C$—) in a process known as auto-oxidation or autoxidation. The acids produced by autoxidation can lower the quality and usefulness of aldehyde-containing compositions.

Despite all of the research and development that has been directed to preservation of aldehydes, there is still a need in the art for improved aldehyde-containing compositions and related methods.

SUMMARY OF THE INVENTION

In an aspect, the present invention provides a novel deuterium-enriched aldehyde of structure 1:

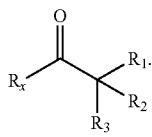

In another aspect, the present invention provides a novel method of making a deuterium-enriched aldehyde of structure 1.

In another aspect, the present invention provides a novel composition, comprising: a deuterium-enriched aldehyde of structure 1.

In another aspect, the present invention provides a novel composition, comprising: a deuterium-enriched aldehyde of structure 1 and an organic solvent.

In another aspect, the present invention provides a novel composition for modulating the behavior of insects, comprising: a deuterium-enriched aldehyde of structure 1 and an optional additional component suitable for the composition.

In another aspect, the present invention provides a novel method of manufacturing a resin or polymer using a deuterium-enriched aldehyde of structure 1.

These and other aspects, which will become apparent during the following detailed description, have been achieved by the inventors' discovery that deuterium can slow the autoxidation of aldehydes.

DETAILED DESCRIPTION OF THE INVENTION

Definitions

Figure 1:
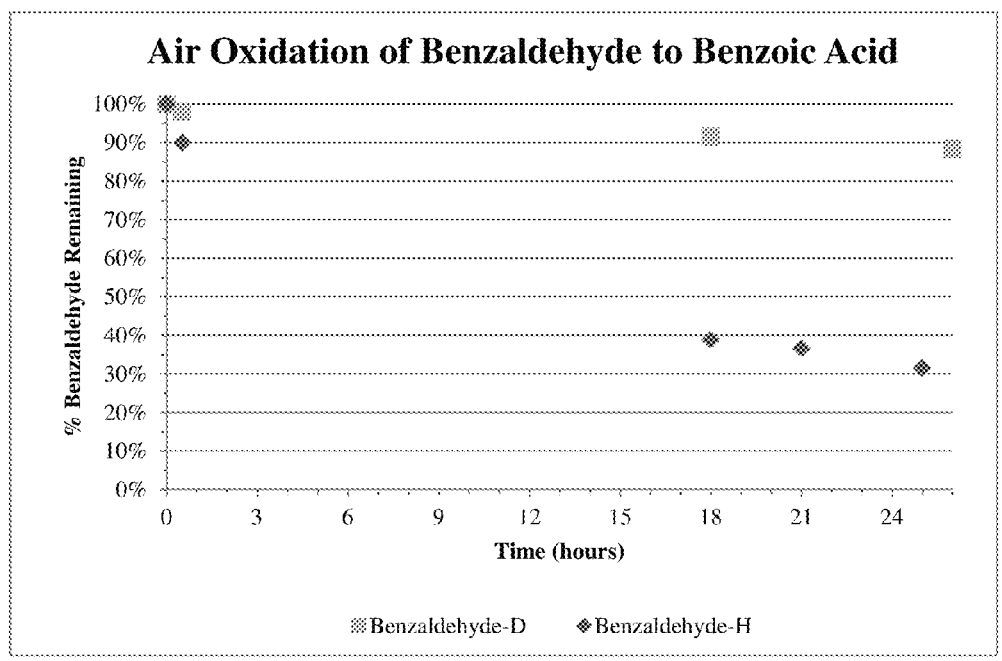
FIG. 1 shows a graph comparing the amount of air oxidation of benzaldehyde to benzoic acid where the hydrogen atom on the carbonyl group (i.e., H—C(O)Ph) is enriched in its deuterium isotope (i.e., >95% deuterium, "benzaldehyde-D") and where it is not enriched (i.e., naturally occurring isotopic abundance, "benzaldehyde-H").
Figure 2:
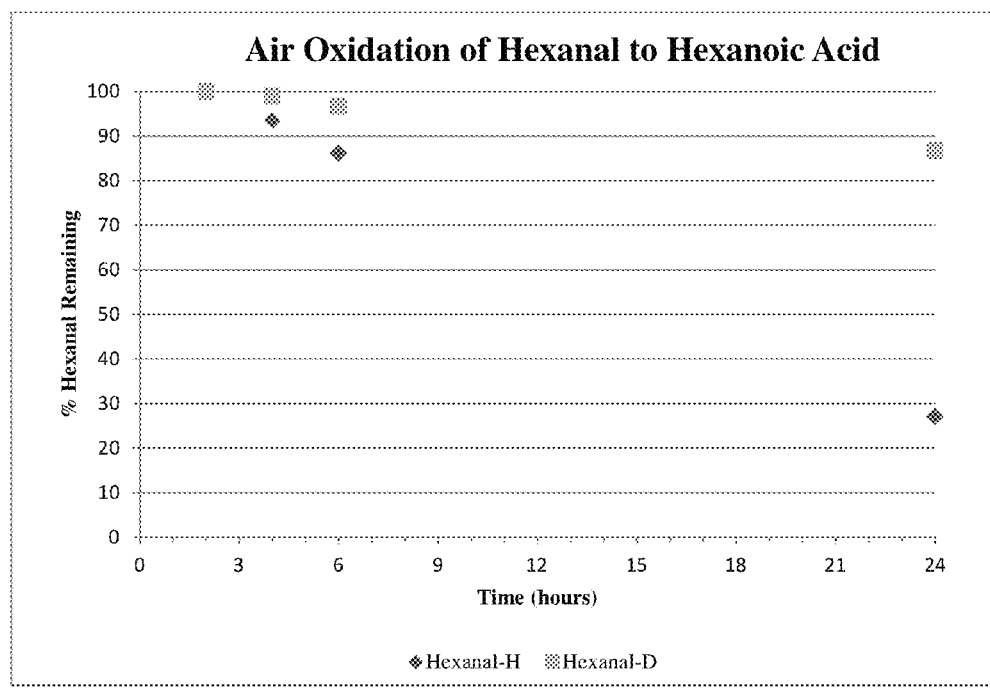
FIG. 2 shows a graph comparing the amount of air oxidation of hexanal to hexanoic acid where the hydrogen atom of the carbonyl group (i.e., H—C(O)$C_5H_{11}$) is enriched in its deuterium isotope (i.e., >95% deuterium, "hexanal-D") and where it is not enriched (i.e., naturally occurring isotopic abundance, "hexanal-H").

All examples provided herein are not intended to be limiting.

"Alkyl" refers to an alkane chemical moiety. The alkanes may be linear, branched, or cyclic. Lower alkyl groups are those that include 1-6 carbon atoms. Higher alkyl groups are those that include 7-20 carbon atoms. Cyclic alkyl or cycloalkyl groups include 3-8 carbon atoms. Examples of such moieties include: $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CH_2CH_2CH_2CH_2CH_3$, $CH(CH_3)CH_2CH_2CH_3$, $CH_2CH(CH_3)CH_2CH_3$, $CH_2CH_2CH(CH_3)_2$, $CH_2CH_2CH_2CH_2CH_3$, cyclopropyl, cyclobutyl, and cyclopentyl.

"Substituted alkyl" refers to an alkyl group where one or more of the hydrogen atoms have been replaced with another chemical group. Examples of such other chemical groups include: halo, OH, $OR_4$ (where $R_4$ is a lower alkyl group), $CF_3$, $OCF_3$, $NH_2$, $NHR_4$ (where $R_4$ is a lower alkyl group), $NR_4R_5$ (where $R_4$ and $R_5$ are independently lower alkyl groups), $CO_2H$, $CO_2R_6$ (where $R_6$ is a lower alkyl group), $C(O)NH_2$, $C(O)NHR_7$ (where $R_7$ is a lower alkyl group), $C(O)NR_7R_8$ (where $R_7$ and $R_8$ are independently lower alkyl groups), CN, alkenyl, substituted alkenyl, alkynyl, substituted alkynyl, aryl, substituted aryl, heteroaryl, and substituted heteroaryl.

"Halo" refers to Cl, F, Br, or I.

"Alkenyl" refers to a moiety containing only carbon and hydrogen that includes at least one double bond. The alkenes may be linear, branched, or cyclic. Lower alkenyl groups are those that include 2-6 carbon atoms. Higher alkenyl groups are those that include 7-20 carbon atoms. Cyclic alkenyl or cycloalkenyl groups include 5-8 carbon atoms. Examples of such moieties include: CH=$CH_2$; CH=$CHCH_3$; $CH_2$CH=CH; CH=$CHCH_2CH_3$; $CH_2$CH=$CHCH_3$; $CH_2CH_2$CH=$CH_2$; CH=$CHCH_2CH_2CH_3$; CH=CHCH$(CH_3)_2$; $CH_2$CH=$CHCH_2CH_3$; $CH_2CH_2$CH=$CHCH_3$; $CH_2CH_2CH_2$CH=$CH_2$; CH=$CHCH_2CH_2CH_3$; CH=$CHCH_2$CH$(CH_3)_2$; cyclopentenyl, and cyclohexenyl.

"Substituted alkenyl" refers to an alkenyl group where one or more of the hydrogen atoms have been replaced with another chemical group. Examples of such other chemical groups include: $CO_2H$, $CO_2R_6$ (where $R_6$ is a lower alkyl group), $C(O)NH_2$, $C(O)NHR_7$ (where $R_7$ is a lower alkyl group), $C(O)NR_7R_8$ (where $R_7$ and $R_8$ are independently lower alkyl groups), CN, alkyl, substituted alkyl, alkynyl, substituted alkynyl, aryl, substituted aryl, heteroaryl, and substituted heteroaryl. Where the replaced hydrogen atom is not on the carbon of the double bond, examples of such other chemical groups further include: halo, OH, $OCH_3$, $CF_3$, $OCF_3$, $NH_2$, $NHR_4$ (where $R_4$ is a lower alkyl group), and $NR_4R_5$ (where $R_4$ and $R_5$ are independently lower alkyl groups).

"Alkynyl" refers to refers to a moiety containing only carbon and hydrogen that includes a triple bond. The alkynes may be linear or branched. Lower alkynyl groups are those that include 2-6 carbon atoms. Higher alkynyl groups are those that include 7-20 carbon atoms. Examples of such moieties include: C≡CH; C≡CCH$_3$; CH$_2$C≡CH; C≡CCH$_2$CH$_3$; CH$_2$C≡CCH$_3$; CH$_2$CH$_2$C≡CH; C≡CCH$_2$CH$_2$CH$_3$; CH$_2$C≡CCH$_2$CH$_3$; CH$_2$CH$_2$C≡CCH$_3$; CH$_2$CH$_2$CH$_2$C≡CH; C≡CCH$_2$CH$_2$CH$_2$CH$_3$; CH$_2$C≡CCH$_2$CH$_2$CH$_3$; CH$_2$CH$_2$C≡CCH$_2$CH$_3$; CH$_2$CH$_2$CH$_2$C≡CCH$_3$; CH$_2$CH$_2$CH$_2$CH$_2$C≡CH; and, C≡CCH$_2$CH(CH$_3$)$_2$.

"Substituted alkynyl" refers to an alkynyl group where one or more of the hydrogen atoms have been replaced with another chemical group. Examples of such other chemical groups include: CO$_2$H, CO$_2$R$_6$ (where R$_6$ is a lower alkyl group), C(O)NH$_2$, C(O)NHR$_7$ (where R$_7$ is a lower alkyl group), C(O)NR$_7$R$_8$ (where R$_7$ and R$_8$ are independently lower alkyl groups), CN, alkyl, substituted alkyl, alkenyl, substituted alkenyl, aryl, substituted aryl, heteroaryl, and substituted heteroaryl. Where the replaced hydrogen atom is not on the carbon of the triple bond, Examples of such other chemical groups further include: halo, OH, OCH$_3$, CF$_3$, OCF$_3$, NH$_2$, NHR$_4$ (where R$_4$ is a lower alkyl group), NR$_4$R$_5$ (where R$_4$ and R$_5$ are independently lower alkyl groups).

"Heteroalkyl" refers to an alkyl group where at least one of the carbon atoms has been replaced with a heteroatom. Examples of heteroatoms include oxygen ("O"), nitrogen ("N") and sulfur ("S"). The heteroalkanes may be linear, branched, or cyclic. Lower heteroalkyl groups are those that include 1-6 carbons and heteroatoms. Higher heteroalkyl groups are those that include 7-20 carbons and heteroatoms. Examples of heteroalkyl groups include: CH$_2$OCH$_3$; CH$_2$CH$_2$OCH$_3$; CH$_2$N(R$_9$)CH$_3$ (where R$_9$ is a lower alkyl group); CH$_2$CH$_2$N(R$_9$)CH$_3$ (where R$_9$ is a lower alkyl group); CH$_2$SCH$_3$; CH$_2$CH$_2$SCH$_3$; tetrahydrofuran, tetrahydropyran, and morpholine.

"Substituted heteroalkyl" refers to a heteroalkyl group where one or more of the hydrogen atoms has been replaced with another chemical group. The hydrogen atom that is replaced is typically not on a carbon atom directly attached to the heteroatom. Examples of such other chemical groups include: halo, OH, OCH$_3$, CF$_3$, OCF$_3$, NH$_2$, NHR$_4$ (where R$_4$ is a lower alkyl group), NR$_4$R$_5$ (where R$_4$ and R$_5$ are independently lower alkyl groups), CO$_2$H, CO$_2$R$_6$ (where R$_6$ is a lower alkyl group), C(O)NH$_2$, C(O)NHR$_7$ (where R$_7$ is a lower alkyl group), C(O)NR$_7$R$_8$ (where R$_7$ and R$_8$ are independently lower alkyl groups), CN, alkyl, aryl, and heteroaryl.

"Aryl" refers to an aromatic group containing only carbon and hydrogen (e.g., C$_6$H$_5$ and C$_{10}$H$_8$).

"Substituted aryl" refers to an aryl group where at least one of the hydrogen atoms has been replaced with another chemical group. Examples of such other chemical groups include: halo, OH, OCH$_3$, CF$_3$, OCF$_3$, NH$_2$, NHR$_4$ (where R$_4$ is a lower alkyl group), NR$_4$R$_5$ (where R$_4$ and R$_5$ are independently lower alkyl groups), CO$_2$H, CO$_2$R$_6$ (where R$_6$ is a lower alkyl group), C(O)NH$_2$, C(O)NHR$_7$ (where R$_7$ is a lower alkyl group), C(O)NR$_7$R$_8$ (where R$_7$ and R$_8$ are independently lower alkyl groups), CN, alkyl, aryl, and heteroaryl.

"Heteroaryl" refers to an aromatic group where at least one of the carbon atoms has been replaced by a heteroatom. Examples of such heteroatoms include oxygen ("O"), nitrogen ("N") and sulfur ("S"). Examples of heteroaryl groups include: C$_4$H$_2$O; C$_4$H$_3$N; C$_4$H$_2$S; and, C$_5$H$_4$N.

"Substituted heteroaryl" refers to a heteroaryl group where at least one of the hydrogen atoms has been replaced with another chemical group. Examples of such other chemical groups include: halo, OH, OCH$_3$, CF$_3$, OCF$_3$, NH$_2$, NHR$_4$ (where R$_4$ is a lower alkyl group), NR$_4$R$_5$ (where R$_4$ and R$_5$ are independently lower alkyl groups), CO$_2$H, CO$_2$R$_6$ (where R$_6$ is a lower alkyl group), C(O)NH$_2$, C(O)NHR$_7$ (where R$_7$ is a lower alkyl group), C(O)NR$_7$R$_8$ (where R$_7$ and R$_8$ are independently lower alkyl groups), CN, aryl, and heteroaryl.

Aspects

In an aspect, the present invention is directed to a deuterium-enriched aldehyde of structure 1:

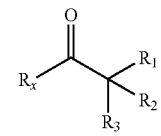

wherein, R$_x$ is hydrogen, wherein the deuterium isotope is in an amount greater than 0.10 percent of the R$_x$ hydrogen atoms. In certain cases, the deuterium isotope comprises greater than 1% of the R$_x$ hydrogen atoms, or greater than 2%, 5%, 10%, 20%, 30%, 40%, 50%, 60%, 70%, 80%, 90%, or 95% percent of the R$_x$ hydrogen atoms. R$_1$, R$_2$ and R$_3$ are independently selected from hydrogen (where the hydrogen is un-enriched (i.e., naturally occurring) or is enriched in its deuterium isotope, e.g., more than 1%, 2%, 5%, 10%, 20%, 30%, 40%, 50%, 60%, 70%, 80%, 90%, or 95%), alkyl, substituted alkyl, alkenyl, substituted alkenyl, alkynyl, substituted alkynyl, heteroalkyl, substituted heteroalkyl, aryl, substituted aryl, heteroaryl, and substituted heteroaryl. Alternatively, the CR$_1$R$_2$R$_3$ moiety forms a group selected from: an aryl, substituted aryl, heteroaryl, and substituted heteroaryl. Alternatively, the CR$_1$R$_2$ moiety forms a group selected from: an alkenyl and substituted alkenyl. Alternatively, the CR$_1$R$_2$R$_3$ moiety forms a group a group selected from: an alkynyl and substituted alkynyl. Optionally, the aldehyde is substituted with C(O)R$_y$, wherein R$_y$ is hydrogen, wherein the deuterium isotope is optionally present in an amount greater than 0.10% of the R$_y$ hydrogen atoms, provided that R$_x$ is optionally H when the deuterium isotope is present in an amount greater than 0.10% of the R$_y$ hydrogen atoms. In certain cases, the deuterium isotope comprises greater than 1% of the R$_y$ hydrogen atoms, or greater than 2%, 5%, 10%, 20%, 30%, 40%, 50%, 60%, 70%, 80%, 90%, or 95% percent of the R$_y$ hydrogen atoms.

In another aspect, the present invention provides a composition, comprising: a deuterium-enriched aldehyde of structure 1:

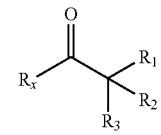

wherein, there are at least 6×10$^{18}$ molecules of the aldehyde, of structure 1. Compositions of the invention will typically comprise at least 6×10$^{19}$ molecules, and may, for example, comprise at least 6×10$^{20}$ molecules, 6×10$^{21}$ molecules, $6\times10^{22}$ molecules, or $6\times10^{23}$ molecules. $R_x$ is hydrogen, wherein the deuterium isotope is in an amount greater than 0.10 percent of the $R_x$ hydrogen atoms. In certain cases, the deuterium isotope comprises greater than 1% of the $R_x$ hydrogen atoms, or greater than 2%, 5%, 10%, 20%, 30%, 40%, 50%, 60%, 70%, 80%, 90%, or 95% percent of the $R_x$ hydrogen atoms. $R_1$, $R_2$ and $R_3$ are independently selected from hydrogen (where the hydrogen is un-enriched (i.e., naturally occurring) or is enriched in its deuterium isotope, e.g., more than 1%, 2%, 5%, 10%, 20%, 30%, 40%, 50%, 60%, 70%, 80%, 90%, or 95%), alkyl, substituted alkyl, alkenyl, substituted alkenyl, alkynyl, substituted alkynyl, heteroalkyl, substituted heteroalkyl, aryl, substituted aryl, heteroaryl, and substituted heteroaryl. Alternatively, the $CR_1R_2R_3$ moiety forms a group selected from: an aryl, substituted aryl, heteroaryl, and substituted heteroaryl. Alternatively, the $CR_1R_2$ moiety forms a group selected from: an alkenyl and substituted alkenyl. Alternatively, the $CR_1R_2R_3$ moiety forms a group a group selected from: an alkynyl and substituted alkynyl. Optionally, the aldehyde is substituted with $C(O)R_y$, wherein $R_y$ is hydrogen, wherein the deuterium isotope is optionally present in an amount greater than 0.10% of the $R_y$ hydrogen atoms, provided that $R_x$ is optionally H when the deuterium isotope is present in an amount greater than 0.10% of the $R_y$ hydrogen atoms. In certain cases, the deuterium isotope comprises greater than 1% of the $R_y$ hydrogen atoms, or greater than 2%, 5%, 10%, 20%, 30%, 40%, 50%, 60%, 70%, 80%, 90%, or 95% percent of the $R_y$ hydrogen atoms.

In another aspect, reference to compositions comprising the "aldehyde of structure 1", means compositions comprising at least 0.1 mole of an aldehyde of structure 1. Compositions of the invention may, for example, comprise at least 0.2, 0.5, 1, 2, 3, 4, 5, 10, or 20 moles of an aldehyde of structure 1.

In another aspect, reference to compositions comprising the "aldehyde of structure 1", means compositions comprising at least 1 gram of an aldehyde of structure 1. Compositions of the invention may, for example, comprise at least 5, 10, 20, 30, 40, 50, 100, 500, or 1,000 grams of an aldehyde of structure 1.

In another aspect, the present invention provides a composition, comprising: a deuterium-enriched aldehyde of structure 1:

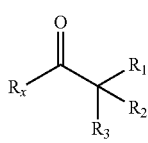

1 wherein:
there are at least $6\times10^{18}$ molecules of the aldehyde;
$R_x$ is hydrogen, wherein the deuterium isotope is present in an amount greater than 0.10% of the $R_x$ hydrogen atoms;
$R_1$, $R_2$ and $R_3$ are independently selected from hydrogen, alkyl, substituted alkyl, alkenyl, substituted alkenyl, alkynyl, substituted alkynyl, heteroalkyl, substituted heteroalkyl, aryl, substituted aryl, heteroaryl, and substituted heteroaryl;
alternatively, the $CR_1R_2R_3$ moiety forms a group selected from: an aryl, substituted aryl, heteroaryl, and substituted heteroaryl;
alternatively, the $CR_1R_2$ moiety forms a group a group selected from: an alkenyl and substituted alkenyl;
alternatively, the $CR_1R_2R_3$ moiety forms a group a group selected from: an alkynyl and substituted alkynyl; and,
optionally, the aldehyde is substituted with $C(O)R_y$, wherein $R_y$ is hydrogen, wherein the deuterium isotope is optionally present in an amount greater than 0.10% of the $R_y$ hydrogen atoms, provided that $R_x$ is optionally H when the deuterium isotope is present in an amount greater than 0.10% of the $R_y$ hydrogen atoms.

The following are examples of aldehydes according to the present invention:

1. A deuterium-enriched aldehyde of structure 1, where $R_1$ and $R_2$ are hydrogen, and $R_3$ is a lower alkyl.
2. A deuterium-enriched aldehyde of structure 1, where $R_1$ and $R_2$ are hydrogen, and $R_3$ is a higher alkyl.
3. A deuterium-enriched aldehyde of structure 1, where $R_1$ and $R_2$ are hydrogen, and $R_3$ is a substituted alkyl, where the substituted alkyl is a lower alkyl, and where the one or more other chemical groups are selected from: halo, OH, $OR_4$ (where $R_4$ is a lower alkyl group), $CF_3$, $OCF_3$, $NH_2$, $NHR_4$ (where $R_4$ is a lower alkyl group), $NR_4R_5$ (where $R_4$ and $R_5$ are independently lower alkyl groups), $CO_2H$, $CO_2R_6$ (where $R_6$ is a lower alkyl group), $C(O)NH_2$, $C(O)NHR_7$ (where $R_7$ is a lower alkyl group), $C(O)NR_7R_8$ (where $R_7$ and $R_8$ are independently lower alkyl groups), CN, aryl, substituted aryl, heteroaryl, and substituted heteroaryl.
4. A deuterium-enriched aldehyde of structure 1, where $R_1$ and $R_2$ are hydrogen, and $R_3$ is a substituted alkyl, where the substituted alkyl is a higher alkyl, and where the one or more other chemical groups are selected from: halo, OH, $OR_4$ (where $R_4$ is a lower alkyl group), $CF_3$, $OCF_3$, $NH_2$, $NHR_4$ (where $R_4$ is a lower alkyl group), $NR_4R_5$ (where $R_4$ and $R_5$ are independently lower alkyl groups), $CO_2H$, $CO_2R_6$ (where $R_6$ is a lower alkyl group), $C(O)NH_2$, $C(O)NHR_7$ (where $R_7$ is a lower alkyl group), $C(O)NR_7R_8$ (where $R_7$ and $R_8$ are independently lower alkyl groups), CN, aryl, substituted aryl, heteroaryl, and substituted heteroaryl.
5. A deuterium-enriched aldehyde of structure 1, where $R_1$ and $R_2$ are hydrogen, and $R_3$ is a lower alkenyl.
6. A deuterium-enriched aldehyde of structure 1, where $R_1$ and $R_2$ are hydrogen, and $R_3$ is a higher alkenyl.
7. A deuterium-enriched aldehyde of structure 1, where $R_1$ and $R_2$ are hydrogen, and $R_3$ is a substituted alkenyl, where the substituted alkenyl is a lower alkenyl, and where the one or more other chemical groups are selected from: $CO_2H$, $CO_2R_6$ (where $R_6$ is a lower alkyl group), $C(O)NH_2$, $C(O)NHR_7$ (where $R_7$ is a lower alkyl group), $C(O)NR_7R_8$ (where $R_7$ and $R_8$ are independently lower alkyl groups), CN, aryl, substituted aryl, heteroaryl, and substituted heteroaryl.
8. A deuterium-enriched aldehyde of structure 1, where $R_1$ and $R_2$ are hydrogen, and $R_3$ is a substituted alkenyl, where the substituted alkenyl is a higher alkenyl, and where the one or more other chemical groups are selected from: $CO_2H$, $CO_2R_6$ (where $R_6$ is a lower alkyl group), $C(O)NH_2$, $C(O)NHR_7$ (where $R_7$ is a lower alkyl group), $C(O)NR_7R_8$ (where $R_7$ and $R_8$ are independently lower alkyl groups), CN, aryl, substituted aryl, heteroaryl, and substituted heteroaryl.
9. A deuterium-enriched aldehyde of structure 1, where $R_1$ and $R_2$ are hydrogen, and $R_3$ is a lower alkynyl.
10. A deuterium-enriched aldehyde of structure 1, where $R_1$ and $R_2$ are hydrogen, and $R_3$ is a higher alkynyl.

11. A deuterium-enriched aldehyde of structure 1, where $R_1$ and $R_2$ are hydrogen, and $R_3$ is a substituted alkynyl, where the substituted alkynyl is a lower alkynyl, and where the chemical groups are selected from: $CO_2H$, $CO_2R_6$ (where $R_6$ is a lower alkyl group), $C(O)NH_2$, $C(O)NHR_7$ (where $R_7$ is a lower alkyl group), $C(O)NR_7R_8$ (where $R_7$ and $R_8$ are independently lower alkyl groups), CN, aryl, substituted aryl, heteroaryl, and substituted heteroaryl.

12. A deuterium-enriched aldehyde of structure 1, where $R_1$ and $R_2$ are hydrogen, and $R_3$ is a substituted alkynyl, where the substituted alkynyl is a higher alkynyl, and where the chemical groups are selected from: $CO_2H$, $CO_2R_6$ (where $R_6$ is a lower alkyl group), $C(O)NH_2$, $C(O)NHR_7$ (where $R_7$ is a lower alkyl group), $C(O)NR_7R_8$ (where $R_7$ and $R_8$ are independently lower alkyl groups), CN, aryl, substituted aryl, heteroaryl, and substituted heteroaryl.

13. A deuterium-enriched aldehyde of structure 1, where $R_1$ and $R_2$ are hydrogen, and $R_3$ is a lower heteroalkyl.

14. A deuterium-enriched aldehyde of structure 1, where $R_1$ and $R_2$ are hydrogen, and $R_3$ is a higher heteroalkyl.

15. A deuterium-enriched aldehyde of structure 1, where $R_1$ and $R_2$ are hydrogen, and $R_3$ is a substituted heteroalkyl, where the substituted heteroalkyl is a lower heteroalkyl.

16. A deuterium-enriched aldehyde of structure 1, where $R_1$ and $R_2$ are hydrogen, and $R_3$ is a substituted heteroalkyl, where the substituted heteroalkyl is a higher heteroalkyl.

17. A deuterium-enriched aldehyde of structure 1, where $R_1$ and $R_2$ are hydrogen, and $R_3$ is aryl.

18. A deuterium-enriched aldehyde of structure 1, where $R_1$ and $R_2$ are hydrogen, and $R_3$ is substituted aryl.

19. A deuterium-enriched aldehyde of structure 1, where $R_1$ and $R_2$ are hydrogen, and $R_3$ is heteroaryl.

20. A deuterium-enriched aldehyde of structure 1, where $CR_1R_2R_3$ is aryl.

21. A deuterium-enriched aldehyde of structure 1, where $CR_1R_2R_3$ is substituted aryl.

22. A deuterium-enriched aldehyde of structure 1, where $CR_1R_2R_3$ is heteroaryl.

23. A deuterium-enriched aldehyde of structure 1, where $CR_1R_2R_3$ is substituted heteroaryl.

24. A deuterium-enriched aldehyde of structure 1, where $CR_1R_2$ is alkenyl and $R_3$ is hydrogen.

25. A deuterium-enriched aldehyde of structure 1, where $CR_1R_2R_3$ is substituted alkenyl and $R_3$ is hydrogen.

26. A deuterium-enriched aldehyde of structure 1, where $CR_1R_2$ is alkenyl and $R_3$ is alkyl.

27. A deuterium-enriched aldehyde of structure 1, where $CR_1R_2R_3$ is substituted alkenyl and $R_3$ is alkyl.

28. A deuterium-enriched aldehyde of structure 1, where $R_1$ is alkyl substituted with $C(O)R_y$.

29. A deuterium-enriched aldehyde of structure 1, where $R_1$ is alkyl substituted with $C(O)R_y$ and $R_2$ and $R_3$ are hydrogens.

30. A deuterium-enriched aldehyde of structure 1, where $CR_1R_2R_3$ aryl substituted with $C(O)R_y$.

31. A deuterium-enriched aldehyde of structure 1, where $CR_1R_2R_3$ substituted aryl substituted with $C(O)R_y$.

Additional deuterium-enriched aldehydes of the present invention include those numbered 2-64 shown below.

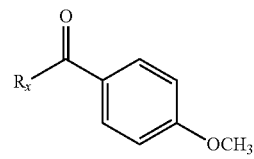

2

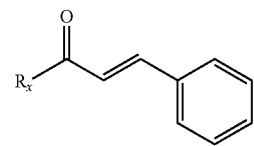

3

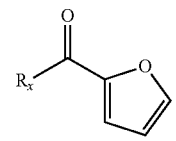

4

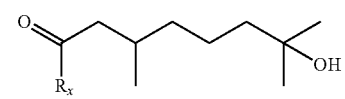

5

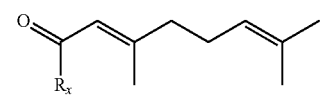

6

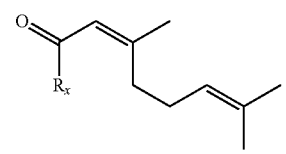

7

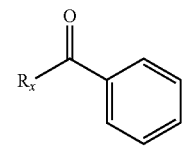

8

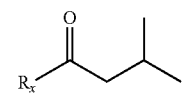

9

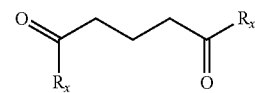

10

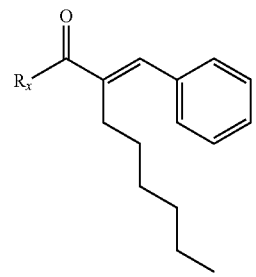

11

-continued
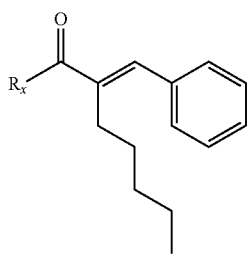
12
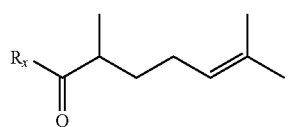
13
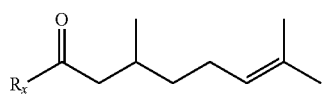
14
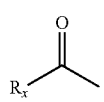
15
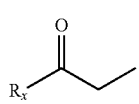
16
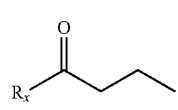
17
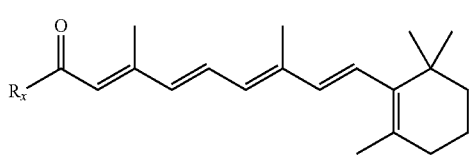
18
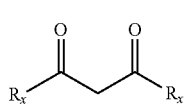
19
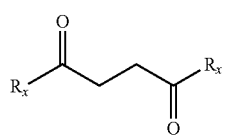
20
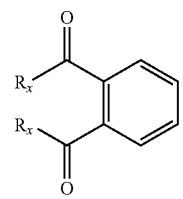
21
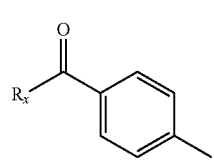
22
-continued
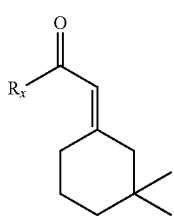
(grandlure IV, E-(3,3-dimethyl)-cyclohexylideneacetaldehyde)
23
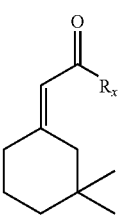
(grandlure III, Z-(3,3-dimethyl)-cyclohexylideneacetaldehyde)
24
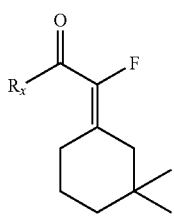
25
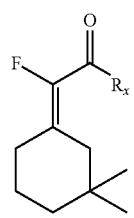
26
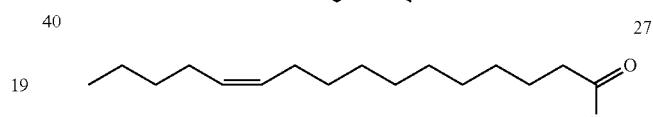
(Z11-16:Ald)
27
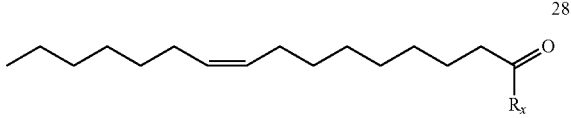
(Z9-16:Ald)
28
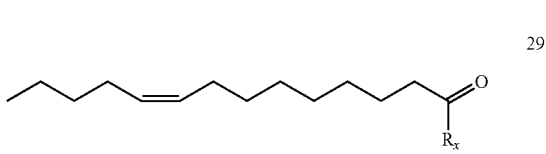
(Z9-14:Ald)
29
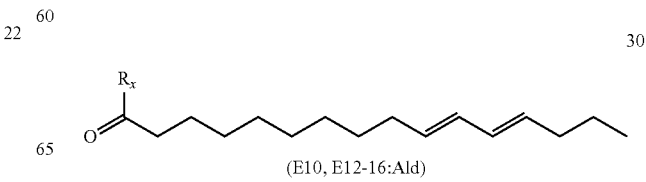
(E10, E12-16:Ald)
30

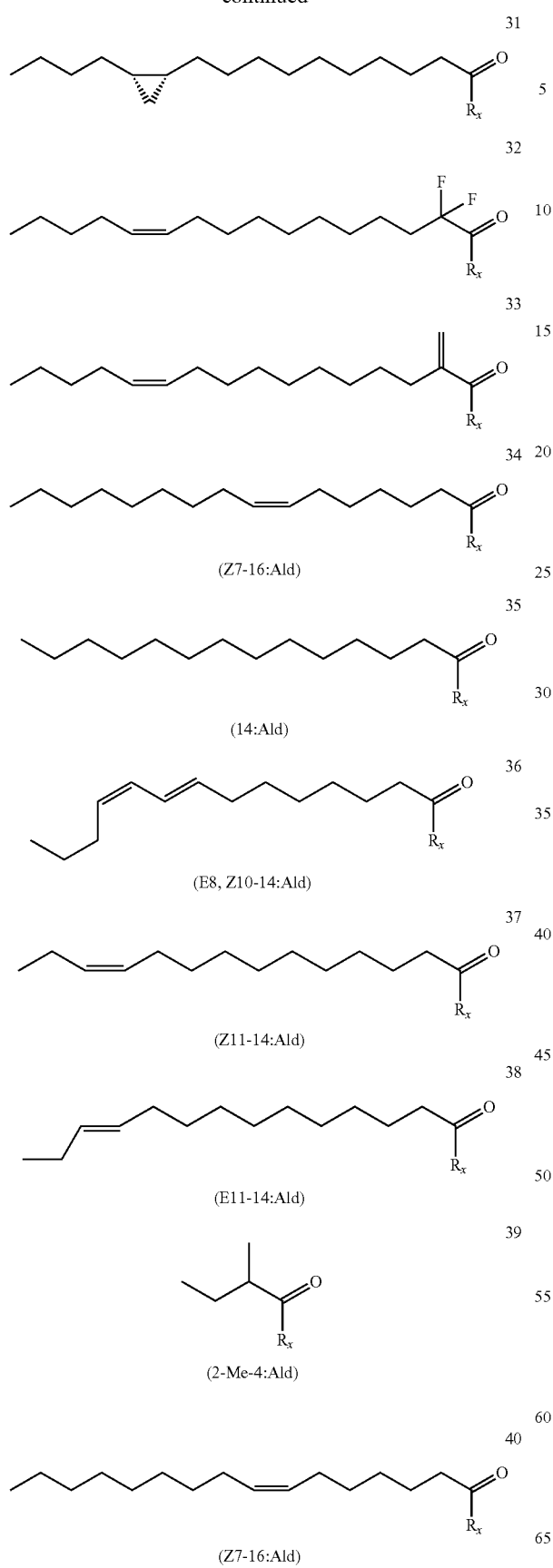
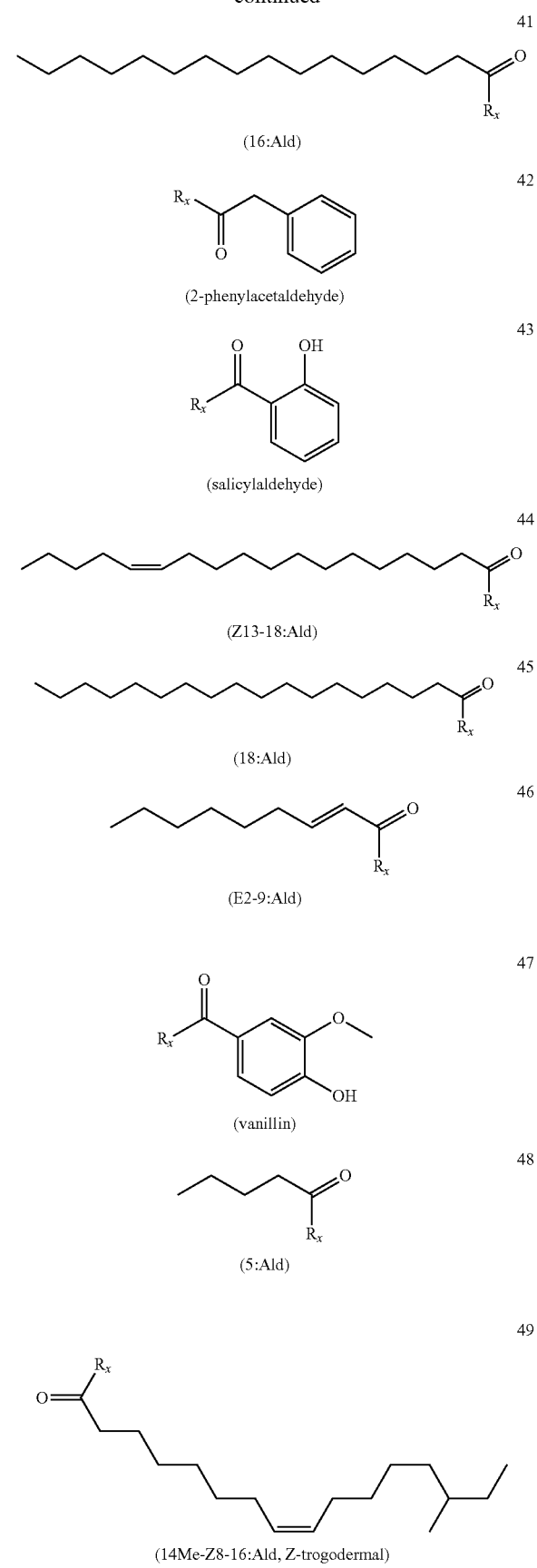

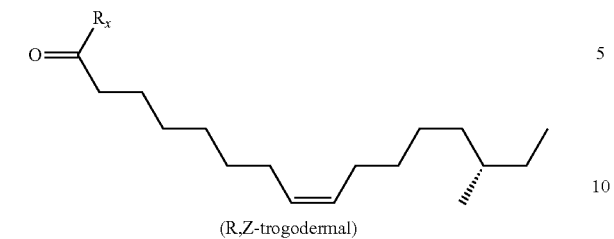
(R,Z-trogodermal)

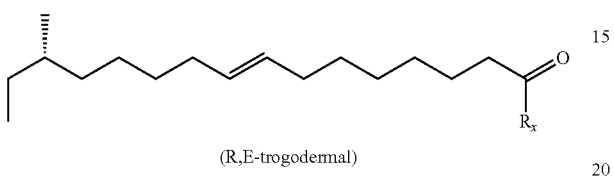
(R,E-trogodermal)

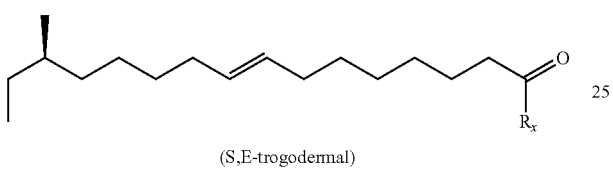
(S,E-trogodermal)

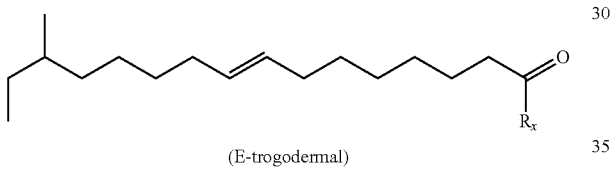
(E-trogodermal)

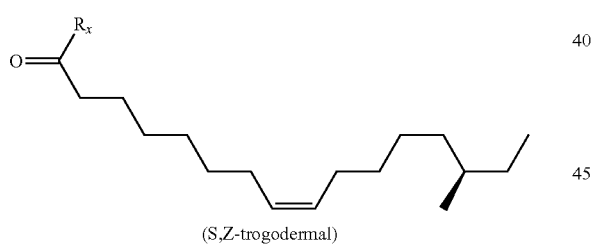
(S,Z-trogodermal)

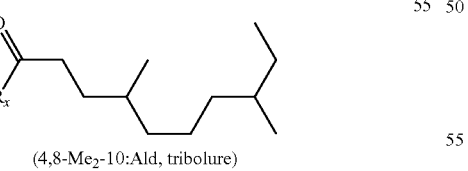
(4,8-Me$_2$-10:Ald, tribolure)

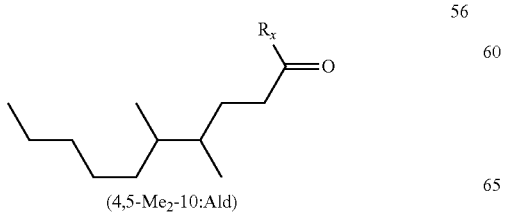
(4,5-Me$_2$-10:Ald)

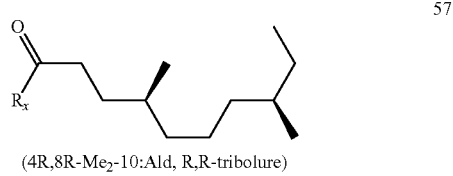
(4R,8R-Me$_2$-10:Ald, R,R-tribolure)

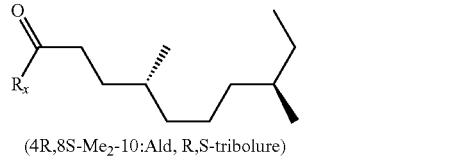
(4R,8S-Me$_2$-10:Ald, R,S-tribolure)

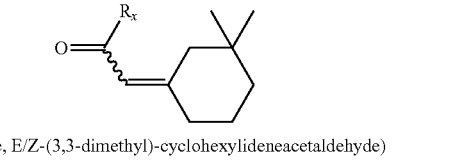
(grandlure, E/Z-(3,3-dimethyl)-cyclohexylideneacetaldehyde)

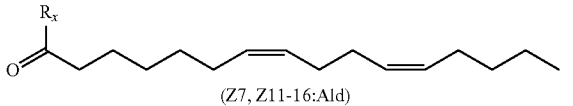
(Z7, Z11-16:Ald)

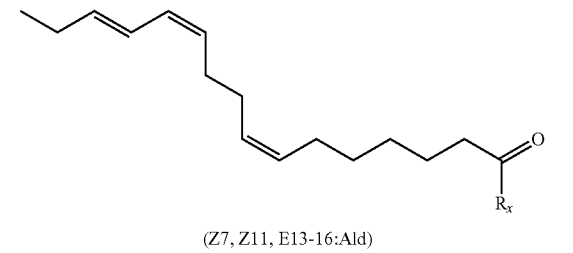
(Z7, Z11, E13-16:Ald)

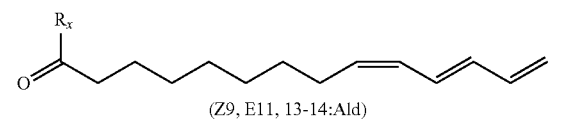
(Z9, E11, 13-14:Ald)

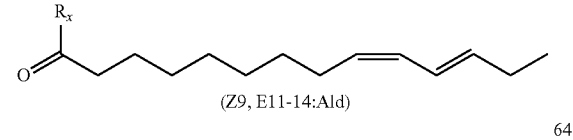
(Z9, E11-14:Ald)

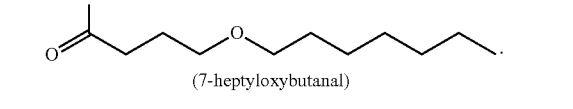
(7-heptyloxybutanal)

Additional deuterium-enriched aldehydes of the present invention include aldehydes 2-64 wherein the deuterium isotope in $R_x$ is in an amount greater than 2% of the hydrogen atoms present in $R_x$.

Additional deuterium-enriched aldehydes of the present invention include aldehydes 2-64 wherein the deuterium isotope in $R_x$ is in an amount greater than 10% of the hydrogen atoms present in $R_x$.

Additional deuterium-enriched aldehydes of the present invention include aldehydes 2-64 wherein the deuterium isotope in $R_x$ is in an amount greater than 20% of the hydrogen atoms present in $R_x$.

Additional deuterium-enriched aldehydes of the present invention include aldehydes 2-64 wherein the deuterium isotope in $R_x$ is in an amount greater than 30% of the hydrogen atoms present in $R_x$.

Additional deuterium-enriched aldehydes of the present invention include aldehydes 2-64 wherein the deuterium isotope in $R_x$ is in an amount greater than 40% of the hydrogen atoms present in $R_x$.

Additional deuterium-enriched aldehydes of the present invention include aldehydes 2-64 wherein the deuterium isotope in $R_x$ is in an amount greater than 50% of the hydrogen atoms present in $R_x$.

Additional deuterium-enriched aldehydes of the present invention include aldehydes 2-64 wherein the deuterium isotope in $R_x$ is in an amount greater than 60% of the hydrogen atoms present in $R_x$.

Additional deuterium-enriched aldehydes of the present invention include aldehydes 2-64 wherein the deuterium isotope in $R_x$ is in an amount greater than 70% of the hydrogen atoms present in $R_x$.

Additional deuterium-enriched aldehydes of the present invention include aldehydes 2-64 wherein the deuterium isotope in $R_x$ is in an amount greater than 80% of the hydrogen atoms present in $R_x$.

Additional deuterium-enriched aldehydes of the present invention include aldehydes 2-64 wherein the deuterium isotope in $R_x$ is in an amount greater than 90% of the hydrogen atoms present in $R_x$.

Additional deuterium-enriched aldehydes of the present invention include aldehydes 2-64 wherein the deuterium isotope in $R_x$ is in an amount greater than 95% of the hydrogen atoms present in $R_x$.

In another aspect, the present invention provides a composition, comprising: a deuterium-enriched aldehyde selected from aldehydes 2-64.

Reference to "compositions comprising compounds 2-64" means compositions comprising at least $6 \times 10^{18}$ molecules of at least one of aldehydes 2-64, typically at least $6 \times 10^{19}$ molecules, and may, for example, comprise at least $6 \times 10^{20}$ molecules, $6 \times 10^{21}$ molecules, $6 \times 10^{22}$ molecules, or $6 \times 10^{23}$ molecules. $R_x$ is hydrogen, wherein the deuterium isotope is in an amount greater than 0.10 percent of the $R_x$ hydrogen atoms. In certain cases, the deuterium isotope comprises greater than 1% of the hydrogen atoms, or even greater than 2%, 5%, 10%, 20%, 30%, 40%, 50%, 60%, 70%, 80%, 90%, or 95% of the hydrogen atoms.

In another aspect, reference to "compositions comprising compounds 2-64" means compositions comprising at least 0.1 mole of at least one of aldehydes 2-64. Compositions of the invention may, for example, comprise at least 0.2, 0.5, 1, 2, 3, 4, 5, 10, to 20 moles of at least one of compounds 2-64.

In another aspect, reference to "compositions comprising compounds 2-64" means compositions comprising at least 1 gram of at least one of aldehydes 2-64. Compositions of the invention may, for example, comprise at least 5, 10, 20, 30, 40, 50, 100, 500, to 1,000 grams of at least one of compounds 2-64.

In another aspect, the present invention provides a composition, comprising: a deuterium-enriched aldehyde selected from aldehydes 2-64 wherein the deuterium isotope in $R_x$ is in an amount greater than 2% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 10% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 20% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 30% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 40% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 50% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 60% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 70% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 80% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 90% of the hydrogen atoms present in $R_x$.

In another aspect, the present invention provides a composition, comprising: a deuterium-enriched aldehyde selected from aldehydes 2-64 wherein the deuterium isotope in $R_x$ is in an amount greater than 95% of the hydrogen atoms present in $R_x$.

Additional deuterium-enriched aldehydes of the present invention include aldehydes 65-358 listed in the Table A below. For each aldehyde listed in the table, the original aldehyde hydrogen (C(O)—H) has been replaced by $R_x$ (C(O)—$R_x$). For example, formaldehyde-$R_x$ (CHO—$R_x$) is HC(O)—$R_x$.

TABLE A

| Ex. | Name | Formula |
|---|---|---|
| 65. | Formaldehyde-$R_x$ | CHO—$R_x$ |
| 66. | 2-Methyl-2-propenal-$R_x$ | $C_4H_5O$—$R_x$ |

TABLE A-continued

| Ex. | Name | Formula |
|---|---|---|
| 67. | 2-Methylpropanal-$R_x$ | $C_4H_7O$—$R_x$ |
| 68. | 2-Propenal-$R_x$ | $C_3H_3O$—$R_x$ |
| 69. | 2-Butenal-$R_x$ | $C_4H_5O$—$R_x$ |
| 70. | 2-Methyl-2-butenal-$R_x$ | $C_5H_7O$—$R_x$ |
| 71. | 2-Methylenebutanal-$R_x$ | $C_5H_7O$—$R_x$ |
| 72. | 3-Methyl-2-butenal-$R_x$ | $C_5H_7O$—$R_x$ |
| 73. | 3-Methyl-3-butenal-$R_x$ | $C_5H_7O$—$R_x$ |
| 74. | 3-Methylbutanal-$R_x$ | $C_5H_9O$—$R_x$ |
| 75. | (E)-2-Pentenal-$R_x$ | $C_5H_7O$—$R_x$ |
| 76. | 2-Methylenepentanal-$R_x$ | $C_6H_9O$—$R_x$ |
| 77. | 2-Pentenal-$R_x$ | $C_5H_7O$—$R_x$ |
| 78. | 3-Methyl-1-(vinyloxy)-butane-$R_x$ | $C_7H_{13}O$—$R_x$ |
| 79. | 4-Methylpentanal-$R_x$ | $C_6H_{11}O$—$R_x$ |
| 80. | Furan-2-carbaldehyde-$R_x$ | $C_5H_3O_2$—$R_x$ |
| 81. | (E)-2-Hexenal-$R_x$ | $C_6H_9O$—$R_x$ |
| 82. | (E)-4-oxo-2-Hexenal-$R_x$ | $C_6H_7O_2$—$R_x$ |
| 83. | (E,E)-2,4-Dimethyl-2,4-hexadienal-$R_x$ | $C_8H_{11}O$—$R_x$ |
| 84. | (E,E)-2,4-Hexadienal-$R_x$ | $C_6H_7O$—$R_x$ |
| 85. | (Z)-2-Hexenal-$R_x$ | $C_6H_9O$—$R_x$ |
| 86. | (Z)-3-Hexenal-$R_x$ | $C_6H_9O$—$R_x$ |
| 87. | (Z)-4-oxo-2-Hexenal-$R_x$ | $C_6H_7O_2$—$R_x$ |
| 88. | 1-Hexenal-$R_x$ | $C_6H_9O$—$R_x$ |
| 89. | 2,3-Dihydroxybenzaldehyde-$R_x$ | $C_7H_5O_3$—$R_x$ |
| 90. | 2-Hexenal-RR | $C_6H_9O$—$R_x$ |
| 91. | 3-((E)-2-Hexenoxy)-hexanal-$R_x$ | $C_{12}H_{21}O_2$—$R_x$ |
| 92. | 3,5-Dimethylhexanal-$R_x$ | $C_8H_{15}O$—$R_x$ |
| 93. | 3-Ethoxyhexanal-$R_x$ | $C_8H_{15}O_2$—$R_x$ |
| 94. | 3-Hydroxybenzaldehyde-$R_x$ | $C_7H_5O_2$—$R_x$ |
| 95. | 3-Hydroxyhexanal-$R_x$ | $C_6H_{11}O_2$—$R_x$ |
| 96. | 4-Hydroxy-3,5-dimethoxybenzaldehyde-$R_x$ | $C_9H_9O_4$—$R_x$ |
| 97. | 4-Hydroxybenzaldehyde-$R_x$ | $C_7H_5O_2$—$R_x$ |
| 98. | 5-Methylhexanal-$R_x$ | $C_7H_{13}O$—$R_x$ |
| 99. | Hexanal-$R_x$ | $C_6H_{11}O$—$R_x$ |
| 100. | (1R,2S,5S)-Iridodial-$R_x$ | $C_{10}H_{15}O_2$—$R_x$ |
| 101. | (1R,5S)-6,6-Dimethylbicyclo[3.1.1]hept-2-ene-2-carbaldehyde-$R_x$ | $C_{10}H_{13}O$—$R_x$ |
| 102. | (1S,2R,3S)-2-(1-Formylvinyl)-5-methylcyclopentanecarbaldehyde-$R_x$ | $C_{10}H_{13}O_2$—$R_x$ |
| 103. | (3S,8R)-2-Methyl-5-(1-formylethyl)-1-cyclopentene-1-carbaldehyde-$R_x$ | $C_{10}H_{13}O_2$—$R_x$ |
| 104. | (3S,8S)-2-Methyl-5-(1-formylethyl)-1-cyclopentene-1-carbaldehyde-$R_x$ | $C_{10}H_{13}O_2$—$R_x$ |
| 105. | (5S,8S)-2-Methyl-5-(1-formylethyl)-1-cyclopentene-1-carbaldehyde-$R_x$ | $C_{10}H_{13}O_2$—$R_x$ |
| 106. | (E)-2-(2-Hydroxyethyl)-6-methyl-2,5-heptadienal-$R_x$ | $C_{10}H_{15}O_2$—$R_x$ |
| 107. | (E)-2-(2-Hydroxyethylidene)-6-methyl-5-heptenal-$R_x$ | $C_{10}H_{15}O_2$—$R_x$ |
| 108. | (E)-2-Heptenal-$R_x$ | $C_7H_{11}O$—$R_x$ |
| 109. | (E)-2-Isopropyl-5-methyl-2-hexenal-$R_x$ | $C_{10}H_{17}O$—$R_x$ |
| 110. | (E,Z)-2,4-Heptadienal-$R_x$ | $C_7H_9O$—$R_x$ |
| 111. | (R)-2-((1R,2R,3S)-3-Methyl-2-vinylcyclopentyl)-propanal-$R_x$ | $C_{11}H_{19}O_2$—$R_x$ |
| 112. | (R)-2-((1S,2S,3S)-3-Methyl-2-vinylcyclopentyl)-propanal-$R_x$ | $C_{11}H_{19}O_2$—$R_x$ |
| 113. | (R)-2,6-Dimethyl-5-heptenal-$R_x$ | $C_9H_{15}O$—$R_x$ |
| 114. | (R)-7-Hydroxy-6,7-dihydro-5H-pyrrolizidine-1-carboxaldehyde-$R_x$ | $C_8H_8NO_2$—$R_x$ |
| 115. | (S)-4-(Prop-1-en-2-yl)-cyclohex-1-enecarbaldehyde-$R_x$ | $C_{10}H_{13}O$—$R_x$ |
| 116. | (S)-7-Hydroxy-6,7-dihydro-5H-pyrrolizidine-1-carboxaldehyde-$R_x$ | $C_8H_8NO_2$—$R_x$ |
| 117. | (Z)-2-Isopropyl-5-methyl-2-hexenal-$R_x$ | $C_{10}H_{17}O$—$R_x$ |
| 118. | 1-Formyl-6,7-dihydro-5H-pyrrolizine-$R_x$ | $C_8H_8NO$—$R_x$ |
| 119. | 1-Formyl-7-hydroxy-6,7-dihydro-5H-pyrrolizine-$R_x$ | $C_9H_{12}NO_2$—$R_x$ |
| 120. | 2-(3-Methylcyclopentyl)-propanal-$R_x$ | $C_9H_{15}O$—$R_x$ |
| 121. | 2,6-Dimethyl-5-heptenal-$R_x$ | $C_9H_{15}O$—$R_x$ |
| 122. | 2-Acetyl-5-methylcyclopentanecarbaldehyde-$R_x$ | $C_9H_{13}O_2$—$R_x$ |
| 123. | 2-Methoxybenzaldehyde-$R_x$ | $C_8H_7O_2$—$R_x$ |
| 124. | 2-Methyl-1-cyclopentenecarboxaldehyde-$R_x$ | $C_7H_9O$—$R_x$ |
| 125. | 3,3-Dimethyl-5-oxo-7-oxabicyclo[4.1.0]heptane-1-carbaldehyde-$R_x$ | $C_9H_{11}O_3$—$R_x$ |
| 126. | 3-Hydroxybenzene-1,2-dicarbaldehyde-$R_x$ | $C_8H_5O_3$—$R_x$ |
| 127. | 3-Methylbenzaldehyde-$R_x$ | $C_8H_7O$—$R_x$ |
| 128. | 4-(Heptyloxy)-butanal-$R_x$ | $C_{11}H_{21}O_2$—$R_x$ |
| 129. | 4-Methoxybenzaldehyde-$R_x$ | $C_8H_7O_2$—$R_x$ |
| 130. | 6,7-Dihydro-5H-pyrrolizine-1-carboxaldehyde-$R_x$ | $C_8H_8NO$—$R_x$ |
| 131. | 6,7-Dihydro-7-oxo-5H-pyrrolizine-1-carbaldehyde-$R_x$ | $C_8H_6NO_2$—$R_x$ |
| 132. | 6-Methylheptanal-Rx | $C_8H_{15}O$—$R_x$ |
| 133. | 7-Hydroxy-6,7-dihydro-5H-pyrrolizin-1-carboxaldehyde-$R_x$ | $C_8H_8NO_2$—$R_x$ |
| 134. | Benzaldehyde-$R_x$ | $C_7H_5O$—$R_x$ |
| 135. | Cyclohexanedial-$R_x$ | $C_8H_{11}O_2$—$R_x$ |
| 136. | Heptanal-$R_x$ | $C_7H_{13}O$—$R_x$ |
| 137. | Plagiodial-$R_x$ | $C_{10}H_{13}O_2$—$R_x$ |
| 138. | (1R,2S)-cis-2-Isopropenyl-1-methylcyclobutaneethanal-$R_x$ | $C_{10}H_{15}O$—$R_x$ |
| 139. | (1R,2S,5R,8R)-Iridodial-$R_x$ | $C_{10}H_{15}O_2$—$R_x$ |
| 140. | (4S)-(3-Oxoprop-1-en-2-yl)-cyclohex-1-enecarbaldehyde-$R_x$ | $C_{10}H_{11}O_2$—$R_x$ |

TABLE A-continued

| Ex. | Name | Formula |
|---|---|---|
| 141. | (E)-2-(3,3-Dimethylcyclohexylidene)-acetaldehyde-$R_x$ | $C_{10}H_{15}O-R_x$ |
| 142. | (E)-2-(4-Methyl-3-pentenyl)-butenedial-$R_x$ | $C_{10}H_{13}O_2-R_x$ |
| 143. | (E)-2-(4-Methyl-3-pentenylidene)-butanedial-$R_x$ | $C_{10}H_{13}O_2-R_x$ |
| 144. | (E)-2,7-Octadienal-$R_x$ | $C_8H_{11}O-R_x$ |
| 145. | (E)-2-Methyl-5-(3-furyl)-2-pentenal-$R_x$ | $C_{10}H_{11}O_2-R_x$ |
| 146. | (E)-2-Octenal-$R_x$ | $C_8H_{13}O-R_x$ |
| 147. | (E)-3,7-Dimethyl-2,6-octadienal-$R_x$ | $C_{10}H_{15}O-R_x$ |
| 148. | (E)-3,7-Dimethyl-2,6-octadienal-$R_x$ | $C_{10}H_{15}O-R_x$ |
| 149. | (E)-4-oxo-2-Octenal-$R_x$ | $C_8H_{11}O_2-R_x$ |
| 150. | (E)-7-Methyl-2-octenal-$R_x$ | $C_9H_{15}O-R_x$ |
| 151. | (E,E)-2,4-Octadienal-$R_x$ | $C_8H_{11}O-R_x$ |
| 152. | (E,E)-2,6-Dimethyl-8-hydroxy-2,6-octadienal-$R_x$ | $C_{10}H_{15}O_2-R_x$ |
| 153. | (E,E)-2,6-Octadienal-$R_x$ | $C_8H_{11}O-R_x$ |
| 154. | (E,E)-2,6-Octadienedial-$R_x$ | $C_8H_9O_2-R_x$ |
| 155. | (E,Z)-2,4-Octadienal-$R_x$ | $C_8H_{11}O-R_x$ |
| 156. | (E,Z)-2,6-Octadienal-$R_x$ | $C_8H_{11}O-R_x$ |
| 157. | (Z)-2-(3,3-Dimethylcyclohexylidene)-acetaldehyde-$R_x$ | $C_{10}H_{15}O-R_x$ |
| 158. | (Z)-3,7-Dimethyl-2,6-octadienal-$R_x$ | $C_{10}H_{15}O-R_x$ |
| 159. | (Z,E)-3,7-Dimethyl-2,6-octadienal-$R_x$ | $C_{10}H_{15}O-R_x$ |
| 160. | 1-Octenal-$R_x$ | $C_8H_{13}O-R_x$ |
| 161. | 2-(1-Formylvinyl)-5-methylcyclopentanecarbaldehyde-$R_x$ | $C_{10}H_{13}O_2-R_x$ |
| 162. | 2,6,6-Trimethyl-1-cyclohexene-1-carbaldehyde-$R_x$ | $C_{10}H_{15}O-R_x$ |
| 163. | 2-Ethyloctanal-$R_x$ | $C_{10}H_{19}O-R_x$ |
| 164. | 2-Hydroxy-6-methylbenzaldehyde-$R_x$ | $C_8H_7O_2-R_x$ |
| 165. | 2-Methyl benzaldehyde-$R_x$ | $C_8H_7O-R_x$ |
| 166. | 2-Octenal-$R_x$ | $C_8H_{13}O-R_x$ |
| 167. | 2-Phenylpropenal-$R_x$ | $C_9H_7O-R_x$ |
| 168. | 3,7-Dimethyl-6-octenal-$R_x$ | $C_{10}H_{17}O-R_x$ |
| 169. | 3-Ethoxy-4-hydroxybenzaldehyde-$R_x$ | $C_9H_9O_3-R_x$ |
| 170. | 3-Ethyl benzaldehyde-$R_x$ | $C_9H_9O-R_x$ |
| 171. | 3-Isopropyl-6-methyl benzaldehyde-$R_x$ | $C_{11}H_{13}O-R_x$ |
| 172. | 3-Octenal-$R_x$ | $C_8H_{13}O-R_x$ |
| 173. | 3-oxo-4-Isopropylidene-1-cyclohexene-1-carboxyaldehyde-$R_x$ | $C_{10}H_{11}O_2-R_x$ |
| 174. | 4-Hydroxy-2-methyl benzaldehyde-$R_x$ | $C_8H_7O_2-R_x$ |
| 175. | 4-Hydroxy-3-methoxybenzaldehyde-$R_x$ | $C_8H_7O_3-R_x$ |
| 176. | 4-Isopropenyl-1-cyclohexene-1-carbaldehyde-$R_x$ | $C_{10}H_{13}O-R_x$ |
| 177. | 4-Isopropenyl-3-oxo-1-cyclohexene-1-carboxyaldehyde-$R_x$ | $C_{10}H_{11}O_2-R_x$ |
| 178. | 4-oxo-Octenal-$R_x$ | $C_8H_{11}O_2-R_x$ |
| 179. | 4S-4-Isopropenyl-3-oxo-1-cyclohexene-1-carboxyaldehyde-$R_x$ | $C_{10}H_{11}O_2-R_x$ |
| 180. | 6,6-Dimethylbicyclo[3.1.1]hept-2-ene-2-carbaldehyde-$R_x$ | $C_{10}H_{13}O-R_x$ |
| 181. | 7-Methyloctanal-$R_x$ | $C_9H_{17}O-R_x$ |
| 182. | Anisomorphal-$R_x$ | $C_{10}H_{13}O_2-R_x$ |
| 183. | cis-2-Isopropenyl-1-methylcyclobutaneethanal-$R_x$ | $C_{10}H_{15}O-R_x$ |
| 184. | Octanal-$R_x$ | $C_8H_{15}O-R_x$ |
| 185. | Peruphasmal-$R_x$ | $C_{10}H_{13}O_2-R_x$ |
| 186. | (E)-4,8-Nonadienal-$R_x$ | $C_9H_{13}O-R_x$ |
| 187. | (E)-8-Methyl-2-nonenal-$R_x$ | $C_{10}H_{17}O-R_x$ |
| 188. | (E,E)-2,4-Nonadienal-$R_x$ | $C_9H_{13}O-R_x$ |
| 189. | (E,E,E)-2,4,6-Nonatrienal-$R_x$ | $C_9H_{11}O-R_x$ |
| 190. | (E,E,Z)-2,4,6-Nonatrienal-$R_x$ | $C_9H_{11}O-R_x$ |
| 191. | (E,Z)-2,6-Nonadienal-$R_x$ | $C_9F1_{13}O-R_x$ |
| 192. | (E,Z,Z)-2,4,6-Nonatrienal-$R_x$ | $C_9H_{11}O-R_x$ |
| 193. | (Z)-3-Nonenal-$R_x$ | $C_9H_{15}O-R_x$ |
| 194. | (Z)-4,8-Nonadienal-$R_x$ | $C_9H_{13}O-R_x$ |
| 195. | (Z)-4-Nonenal-$R_x$ | $C_9H_{15}O-R_x$ |
| 196. | (Z)-8-Methyl-2-nonenal-$R_x$ | $C_{10}H_{17}O-R_x$ |
| 197. | 2-Phenyl-2-butenal-$R_x$ | $C_{10}H_9O-R_x$ |
| 198. | 3-(4-Methoxyphenyl)-2-propenal-$R_x$ | $C_{10}H_9O_2-R_x$ |
| 199. | 3-Phenyl-2-propenal-$R_x$ | $C_9H_7O-R_x$ |
| 200. | 3-Phenylpropanal-$R_x$ | $C_9H_9O-R_x$ |
| 201. | 6-Ethyl benzaldehyde-$R_x$ | $C_9H_9O-R_x$ |
| 202. | 8-Methylnonanal-$R_x$ | $C_{10}H_{19}O-R_x$ |
| 203. | 9-Acetyloxynonanal-$R_x$ | $C_{11}H_{19}O_3-R_x$ |
| 204. | Nonanal-$R_x$ | $C_9H_{17}O-R_x$ |
| 205. | (E)-2,9-Decadienal-$R_x$ | $C_{10}H_{15}O-R_x$ |
| 206. | (E)-2-Decenal-$R_x$ | $C_{10}H_{17}O-R_x$ |
| 207. | (E)-4-oxo-2-Decenal-$R_x$ | $C_{10}H_{15}O_2-R_x$ |
| 208. | (E)-8-Hydroxy-4,8-dimethyl-4,9-decadienal-$R_x$ | $C_{12}H_{19}O_2-R_x$ |
| 209. | (E)-9-Methyl-2-decenal-$R_x$ | $C_{11}H_{19}O-R_x$ |
| 210. | (E,E)-2,4-Decadienal-$R_x$ | $C_{10}H_{15}O-R_x$ |
| 211. | (E,Z)-2,4-Decadienal-$R_x$ | $C_{10}H_{15}O-R_x$ |
| 212. | (Z)-4-Decenal-$R_x$ | $C_{10}H_{17}O-R_x$ |
| 213. | (Z)-5-Decenal-$R_x$ | $C_{10}H_{17}O-R_x$ |
| 214. | (Z)-9-Methyl-2-decenal-$R_x$ | $C_{11}H_{19}O-R_x$ |
| 215. | 1-Decenal-$R_x$ | $C_{10}H_{17}O-R_x$ |
| 216. | 2-Decenal-$R_x$ | $C_{10}H_{17}O-R_x$ |
| 217. | 2-Ethyldecanal-$R_x$ | $C_{12}H_{23}O-R_x$ |
| 218. | Decanal-$R_x$ | $C_{10}H_{19}O-R_x$ |

TABLE A-continued

| Ex. | Name | Formula |
|---|---|---|
| 219. | (5E)-2,6,10-Trimethylundeca-5,9-dienal-$R_x$ | $C_{14}H_{23}O$—$R_x$ |
| 220. | (E)-2-Undecenal-$R_x$ | $C_{11}H_{19}O$—$R_x$ |
| 221. | (E)-6-Ethyl-2,10-dimethyl-5,9-undecadienal-$R_x$ | $C_{15}H_{25}O$—$R_x$ |
| 222. | 10-Undecenal-$R_x$ | $C_{11}H_{19}O$—$R_x$ |
| 223. | 2-Butyl-2-octenal-$R_x$ | $C_{12}H_{21}O$—$R_x$ |
| 224. | 5-Methyl-2-phenyl-2-hexenal-$R_x$ | $C_{13}H_{15}O$—$R_x$ |
| 225. | 8-Isopropyl-5-methyl-3,4,4a,5,6,7,8,8a-octahydronaphthalene-2-carbaldehyde-$R_x$ | $C_{15}H_{23}O$—$R_x$ |
| 226. | syn-4,6-Dimethylundecanal-$R_x$ | $C_{13}H_{25}O$—$R_x$ |
| 227. | Undecanal-$R_x$ | $C_{11}H_{21}O$—$R_x$ |
| 228. | (3R,5R,9R)-3,5,9-Trimethyldodecanal-$R_x$ | $C_{15}H_{29}O$—$R_x$ |
| 229. | (3S,6E)-7-Ethyl-3,11-dimethyldodeca-6,10-dienal-$R_x$ | $C_{16}H_{27}O$—$R_x$ |
| 230. | (9R)-3,5,9-Trimethyldodecanal-$R_x$ | $C_{15}H_{29}O$—$R_x$ |
| 231. | (E)-10-Dodecenal-$R_x$ | $C_{12}H_{21}O$—$R_x$ |
| 232. | (E)-2-Dodecenal-$R_x$ | $C_{12}H_{21}O$—$R_x$ |
| 233. | (E)-3,7,11-Trimethyl-6,10-dodecadienal-$R_x$ | $C_{15}H_{25}O$—$R_x$ |
| 234. | (E)-6-Dodecenal-$R_x$ | $C_{12}H_{21}O$—$R_x$ |
| 235. | (E)-7-Dodecenal-$R_x$ | $C_{12}H_{21}O$—$R_x$ |
| 236. | (E)-8-Dodecenal-$R_x$ | $C_{12}H_{21}O$—$R_x$ |
| 237. | (E)-9,11-Dodecadienal-$R_x$ | $C_{12}H_{19}O$—$R_x$ |
| 238. | (E)-9-Dodecenal-$R_x$ | $C_{12}H_{21}O$—$R_x$ |
| 239. | (E,E)-3,7,11-Trimethyl-2,6,10-dodecatrienal-$R_x$ | $C_{15}H_{23}O$—$R_x$ |
| 240. | (E,E)-7-Ethyl-3,11-dimethyl-2,6,10-dodecatrienal-$R_x$ | $C_{16}H_{25}O$—$R_x$ |
| 241. | (E,E)-8,10-Dodecadienal-$R_x$ | $C_{12}H_{19}O$—$R_x$ |
| 242. | (E,E,E)-3,7-Dimethyl-8,11-dioxo-2,6,9-dodecatrienal-$R_x$ | $C_{14}H_{17}O_3$—$R_x$ |
| 243. | (E,E,Z)-3,7-Dimethyl-8,11-dioxo-2,6,9-dodecatrienal-$R_x$ | $C_{14}H_{17}O_3$—$R_x$ |
| 244. | (E,Z)-5,7-Dodecadienal-$R_x$ | $C_{12}H_{19}O$—$R_x$ |
| 245. | (E,Z)-7,9-Dodecadienal-$R_x$ | $C_{12}H_{19}O$—$R_x$ |
| 246. | (E,Z)-8,10-Dodecadienal-$R_x$ | $C_{12}H_{19}O$—$R_x$ |
| 247. | (S,E)-3,7,11-Trimethyl-6,10-dodecadienal-$R_x$ | $C_{15}H_{25}O$—$R_x$ |
| 248. | (Z)-2-Methyl-5-((1R,5R,6S)-2,6-dimethylbicyclo[3.1.1]hept-2-en-6-yl)-pent-2-enal-$R_x$ | $C_{15}H_{21}O$—$R_x$ |
| 249. | (Z)-5-Dodecenal-$R_x$ | $C_{12}H_{21}O$—$R_x$ |
| 250. | (Z)-7-Dodecenal-$R_x$ | $C_{12}H_{21}O$—$R_x$ |
| 251. | (Z)-9,11-Dodecadienal-$R_x$ | $C_{12}H_{19}O$—$R_x$ |
| 252. | (Z)-9-Dodecenal-$R_x$ | $C_{12}H_{21}O$—$R_x$ |
| 253. | (Z,E)-3,7,11-Trimethyl-2,6,10-dodecatrienal-$R_x$ | $C_{15}H_{23}O$—$R_x$ |
| 254. | (Z,E)-5,7-Dodecadienal-$R_x$ | $C_{12}H_{19}O$—$R_x$ |
| 255. | (Z,E)-7-Ethyl-3,11-dimethyl-2,6,10-dodecatrienal-$R_x$ | $C_{16}H_{25}O$—$R_x$ |
| 256. | (Z,E)-8,10-Dodecadienal-$R_x$ | $C_{12}H_{19}O$—$R_x$ |
| 257. | (Z,Z)-5,7-Dodecadienal-$R_x$ | $C_{12}H_{19}O$—$R_x$ |
| 258. | 2-Ethyldodecanal-$R_x$ | $C_{14}H_{27}O$—$R_x$ |
| 259. | 3,7,11-Trimethyl-(E)-6,10-dodecadienal-$R_x$ | $C_{15}H_{25}O$—$R_x$ |
| 260. | Dodecanal-$R_x$ | $C_{12}H_{23}O$—$R_x$ |
| 261. | syn-4,6-Dimethyldodecanal-$R_x$ | $C_{14}H_{27}O$—$R_x$ |
| 262. | (3S,4R,6E,10Z)-3,4,7,11-Tetramethyl-6,10-tridecadienal-$R_x$ | $C_{17}H_{29}O$—$R_x$ |
| 263. | (Z)-4-Tridecenal-$R_x$ | $C_{13}H_{23}O$—$R_x$ |
| 264. | 13-Acetyloxytridecanal-$R_x$ | $C_{15}H_{27}O_3$—$R_x$ |
| 265. | Tridecanal-$R_x$ | $C_{13}H_{25}O$—$R_x$ |
| 266. | (E)-11,13-Tetradecadienal-$R_x$ | $C_{14}H_{23}O$—$R_x$ |
| 267. | (E,E)-8,10-Tetradecadienal-$R_x$ | $C_{14}H_{23}O$—$R_x$ |
| 268. | (E,Z)-4,9-Tetradecadienal-$R_x$ | $C_{14}H_{23}O$—$R_x$ |
| 269. | (Z)-11,13-Tetradecadienal-$R_x$ | $C_{14}H_{23}O$—$R_x$ |
| 270. | (Z)-5-Tetradecenal-$R_x$ | $C_{14}H_{25}O$—$R_x$ |
| 271. | (Z)-7-Tetradecenal-$R_x$ | $C_{14}H_{25}O$—$R_x$ |
| 272. | (Z)-9,13-Tetradecadien-11-ynal-$R_x$ | $C_{14}H_{19}O$—$R_x$ |
| 273. | (Z,E)-9,12-Tetradecadienal-$R_x$ | $C_{14}H_{23}O$—$R_x$ |
| 274. | (Z,Z)-8,10-Tetradecadienal-$R_x$ | $C_{14}H_{23}O$—$R_x$ |
| 275. | (Z,Z)-9,11-Tetradecadienal-$R_x$ | $C_{14}H_{23}O$—$R_x$ |
| 276. | 10,12-Tetradecadienal-$R_x$ | $C_{14}H_{23}O$—$R_x$ |
| 277. | 2-Ethyltetradecanal-$R_x$ | $C_{16}H_{31}O$—$R_x$ |
| 278. | 3-oxo-13-Tetradecenal-$R_x$ | $C_{14}H_{23}O_2$—$R_x$ |
| 279. | 3-oxo-Tetradecanal-$R_x$ | $C_{14}H_{25}O_2$—$R_x$ |
| 280. | 5,8-Tetradecadienal-$R_x$ | $C_{14}H_{23}O$—$R_x$ |
| 281. | 5-Tetradecenal-$R_x$ | $C_{14}H_{25}O$—$R_x$ |
| 282. | (E)-5,9-Dimethyl-2-(6-methylhept-5-en-2-yl)-deca-4,8-dienal-$R_x$ | $C_{20}H_{33}O$—$R_x$ |
| 283. | (E,Z)-9,11-Pentadecadienal-$R_x$ | $C_{15}H_{25}O$—$R_x$ |
| 284. | (Z)-10-Pentadecenal-$R_x$ | $C_{15}H_{27}O$—$R_x$ |
| 285. | (Z)-6,14-Pentadecadienal-$R_x$ | $C_{15}H_{25}O$—$R_x$ |
| 286. | (Z,Z)-9,11-Pentadecadienal-$R_x$ | $C_{15}H_{25}O$—$R_x$ |
| 287. | 2-Hexyl-2-decenal-$R_x$ | $C_{16}H_{29}O$—$R_x$ |
| 288. | Pentadecanal-$R_x$ | $C_{15}H_{29}O$—$R_x$ |
| 289. | (1R)-Pimaral-$R_x$ | $C_{20}H_{29}O$—$R_x$ |
| 290. | (E)-10-Hexadecenal-$R_x$ | $C_{16}H_{29}O$—$R_x$ |
| 291. | (E)-11-Hexadecenal-$R_x$ | $C_{16}H_{29}O$—$R_x$ |
| 292. | (E,E)-10,14-Hexadecadienal-$R_x$ | $C_{16}H_{27}O$—$R_x$ |
| 293. | (E,E)-11,13-Hexadecadienal-$R_x$ | $C_{16}H_{27}O$—$R_x$ |
| 294. | (E,E)-9,11-Hexadecadienal-$R_x$ | $C_{16}H_{27}O$—$R_x$ |

TABLE A-continued

| Ex. | Name | Formula |
|---|---|---|
| 295. | (E,E,E)-10,12,14-Hexadecatrienal-$R_x$ | $C_{16}H_{25}O-R_x$ |
| 296. | (E,E,E)-3,7,11,15-tetramethyl-2,6,10,14-hexadecatetraenal-$R_x$ | $C_{20}H_{31}O-R_x$ |
| 297. | (E,E,Z)-10,12,14-Hexadecatrienal-$R_x$ | $C_{16}H_{25}O-R_x$ |
| 298. | (E,E,Z)-4,6,11-Hexadecatrienal-$R_x$ | $C_{16}H_{25}O-R_x$ |
| 299. | (E,E,Z,Z)-4,6,11,13-Hexadecatetraenal-$R_x$ | $C_{16}H_{23}O-R_x$ |
| 300. | (E,Z)-10,12-Hexadecadienal-$R_x$ | $C_{16}H_{27}O-R_x$ |
| 301. | (E,Z)-11,13-Hexadecadienal-$R_x$ | $C_{16}H_{27}O-R_x$ |
| 302. | (E,Z)-4,6-Hexadecadienal-$R_x$ | $C_{16}H_{27}O-R_x$ |
| 303. | (E,Z)-6,11-Hexadecadienal-$R_x$ | $C_{16}H_{27}O-R_x$ |
| 304. | (E,Z)-8,11-Hexadecadienal-$R_x$ | $C_{16}H_{27}O-R_x$ |
| 305. | (E,Z)-9,11-Hexadecadienal-$R_x$ | $C_{16}H_{27}O-R_x$ |
| 306. | (Z)-10-Hexadecenal-$R_x$ | $C_{16}H_{29}O-R_x$ |
| 307. | (Z)-12-Hexadecenal-$R_x$ | $C_{16}H_{29}O-R_x$ |
| 308. | (Z)-13-Hexadecen-11-ynal-$R_x$ | $C_{16}H_{25}O-R_x$ |
| 309. | (Z)-3-oxo-9-Hexadecenal-$R_x$ | $C_{16}H_{27}O_2-R_x$ |
| 310. | (Z,E)-10,12-Hexadecadienal-$R_x$ | $C_{16}H_{27}O-R_x$ |
| 311. | (Z,E)-11,13-Hexadecadienal-$R_x$ | $C_{16}H_{27}O-R_x$ |
| 312. | (Z,E)-7,11-Hexadecadienal-$R_x$ | $C_{16}H_{27}O-R_x$ |
| 313. | (Z,E)-9,11-Hexadecadienal-$R_x$ | $C_{16}H_{27}O-R_x$ |
| 314. | (Z,Z)-10,12-Hexadecadienal-$R_x$ | $C_{16}H_{27}O-R_x$ |
| 315. | (Z,Z)-11,13-Hexadecadienal-$R_x$ | $C_{16}H_{27}O-R_x$ |
| 316. | (Z,Z)-9,11-Hexadecadienal-$R_x$ | $C_{16}H_{27}O-R_x$ |
| 317. | 11-Hexadecynal-$R_x$ | $C_{16}H_{27}O-R_x$ |
| 318. | 2-Methylhexadecanal-$R_x$ | $C_{17}H_{33}O-R_x$ |
| 319. | 7-Hexadecenal-$R_x$ | $C_{16}H_{29}O-R_x$ |
| 320. | 9-Hexadecenal-$R_x$ | $C_{16}H_{29}O-R_x$ |
| 321. | (Z)-9-Heptadecenal-$R_x$ | $C_{17}H_{31}O-R_x$ |
| 322. | 1-Heptadecenal-$R_x$ | $C_{17}H_{31}O-R_x$ |
| 323. | 2-Heptadecenal-$R_x$ | $C_{17}H_{31}O-R_x$ |
| 324. | Heptadecanal-$R_x$ | $C_{17}H_{33}O-R_x$ |
| 325. | (E)-11-Octadecenal-$R_x$ | $C_{18}H_{33}O-R_x$ |
| 326. | (E)-13-Octadecenal-$R_x$ | $C_{18}H_{33}O-R_x$ |
| 327. | (E)-14-Octadecenal-$R_x$ | $C_{18}H_{33}O-R_x$ |
| 328. | (E)-2-Octadecenal-$R_x$ | $C_{18}H_{33}O-R_x$ |
| 329. | (E,E)-11,14-Octadecadienal-$R_x$ | $C_{18}H_{31}O-R_x$ |
| 330. | (E,Z)-2,13-Octadecadienal-$R_x$ | $C_{18}H_{31}O-R_x$ |
| 331. | (E,Z)-3,13-Octadecadienal-$R_x$ | $C_{18}H_{31}O-R_x$ |
| 332. | (Z)-11-Octadecenal-$R_x$ | $C_{18}H_{33}O-R_x$ |
| 333. | (Z)-13-Octadecenal-$R_x$ | $C_{18}H_{33}O-R_x$ |
| 334. | (Z)-9-Octadecenal-$R_x$ | $C_{18}H_{33}O-R_x$ |
| 335. | (Z,Z)-11,13-Octadecadienal-$R_x$ | $C_{18}H_{31}O-R_x$ |
| 336. | (Z,Z)-13,15-Octadecadienal-$R_x$ | $C_{18}H_{31}O-R_x$ |
| 337. | (Z,Z)-3,13-Octadecadienal-$R_x$ | $C_{18}H_{31}O-R_x$ |
| 338. | (Z,Z)-9,12-Octadecadienal-$R_x$ | $C_{18}H_{31}O-R_x$ |
| 339. | (Z,Z,Z)-9,12,15-Octadecatrienl-$R_x$ | $C_{18}H_{29}O-R_x$ |
| 340. | 1-Octadecenal-$R_x$ | $C_{18}H_{33}O-R_x$ |
| 341. | 9-Octadecenal-$R_x$ | $C_{18}H_{33}O-R_x$ |
| 342. | Octadecanal-$R_x$ | $C_{18}H_{35}O-R_x$ |
| 343. | (Z)-10-Nonadecenal-$R_x$ | $C_{19}H_{35}O-R_x$ |
| 344. | (Z)-9-Nonadecenal-$R_x$ | $C_{19}H_{35}O-R_x$ |
| 345. | (Z)-11-Eicosenal-$R_x$ | $C_{20}H_{37}O-R_x$ |
| 346. | 12-Deacetoxy-12-oxo-scalaradial-$R_x$ | $C_{25}H_{35}O_3-R_x$ |
| 347. | 1-Eicosenal-$R_x$ | $C_{20}H_{37}O-R_x$ |
| 348. | Deacetylscalaraial-$R_x$ | $C_{25}H_{37}O_3-R_x$ |
| 349. | Eicosanal-$R_x$ | $C_{20}H_{39}O-R_x$ |
| 350. | Scalaradial-$R_x$ | $C_{27}H_{39}O_4-R_x$ |
| 351. | Docosanal-$R_x$ | $C_{22}H_{43}O-R_x$ |
| 352. | Tetracosanal-$R_x$ | $C_{24}H_{47}O-R_x$ |
| 353. | Pentacosanal-$R_x$ | $C_{25}H_{49}O-R_x$ |
| 354. | Hexacosanal-$R_x$ | $C_{26}H_{51}O-R_x$ |
| 355. | Heptacosanal-$R_x$ | $C_{27}H_{53}O-R_x$ |
| 356. | Octacosanal-$R_x$ | $C_{28}H_{55}O-R_x$ |
| 357. | Triacontanal-$R_x$ | $C_{30}H_{59}O-R_x$ |
| 358. | Dotriacontanal-$R_x$ | $C_{32}H_{63}O-R_x$ |

Additional deuterium-enriched aldehydes of the present invention include aldehydes 65-358 listed in the Tables B-L below.

Table B: Examples 64-358 of Table A, except that the deuterium isotope in $R_x$ is in an amount greater than 2% of the hydrogen atoms present in $R_x$.

Table C: Examples 64-358 of Table A, except that the deuterium isotope in $R_x$ is in an amount greater than 10% of the hydrogen atoms present in $R_x$.

Table D: Examples 64-358 of Table A, except that the deuterium isotope in $R_x$ is in an amount greater than 20% of the hydrogen atoms present in $R_x$.

Table E: Examples 64-358 of Table A, except that the deuterium isotope in $R_x$ is in an amount greater than 30% of the hydrogen atoms present in $R_x$.

Table F: Examples 64-358 of Table A, except that the deuterium isotope in $R_x$ is in an amount greater than 40% of the hydrogen atoms present in $R_x$.

Table G: Examples 64-358 of Table A, except that the deuterium isotope in $R_x$ is in an amount greater than 50% of the hydrogen atoms present in $R_x$.

Table H: Examples 64-358 of Table A, except that the deuterium isotope in $R_x$ is in an amount greater than 60% of the hydrogen atoms present in $R_x$.

Table I: Examples 64-358 of Table A, except that the deuterium isotope in $R_x$ is in an amount greater than 70% of the hydrogen atoms present in $R_x$.

Table J: Examples 64-358 of Table A, except that the deuterium isotope in $R_x$ is in an amount greater than 80% of the hydrogen atoms present in $R_x$.

Table K: Examples 64-358 of Table A, except that the deuterium isotope in $R_x$ is in an amount greater than 90% of the hydrogen atoms present in $R_x$.

Table L: Examples 64-358 of Table A, except that the deuterium isotope in $R_x$ is in an amount greater than 95% of the hydrogen atoms present in $R_x$.

In another aspect, the present invention provides a composition, comprising: a deuterium-enriched aldehyde selected from aldehydes 65-358 of Table A.

Reference to "compositions comprising compounds 65-358" means compositions comprising at least $6 \times 10^{18}$ molecules of at least one of aldehydes 65-358, typically at least $6 \times 10^{19}$ molecules, and may, for example, comprise at least $6 \times 10^{20}$ molecules, $6 \times 10^{21}$ molecules, $6 \times 10^{22}$ molecules, or $6 \times 10^{23}$ molecules. $R_x$ is hydrogen, wherein the deuterium isotope is in an amount greater than 0.10 percent of the $R_x$ hydrogen atoms. In certain cases, the deuterium isotope comprises greater than 1% of the hydrogen atoms, or even greater than 2%, 5%, 10%, 20%, 30%, 40%, 50%, 60%, 70%, 80%, 90%, or 95% of the hydrogen atoms.

In another aspect, reference to "compositions comprising compounds 65-358" means compositions comprising at least 0.1 mole of at least one of aldehydes 65-358. Compositions of the invention may, for example, comprise at least 0.2, 0.5, 1, 2, 3, 4, 5, 10, to 20 moles of at least one of compounds 65-358.

In another aspect, reference to "compositions comprising compounds 65-358" means compositions comprising at least 1 gram of at least one of aldehydes 65-358. Compositions of the invention may, for example, comprise at least 5, 10, 20, 30, 40, 50, 100, 500, to 1,000 grams of at least one of compounds 65-358.

In another aspect, the present invention provides a composition, comprising: a deuterium-enriched aldehyde selected from aldehydes 65-358 of Table B.

In another aspect, the present invention provides a composition, comprising: a deuterium-enriched aldehyde selected from aldehydes 65-358 of Table C.

In another aspect, the present invention provides a composition, comprising: a deuterium-enriched aldehyde selected from aldehydes 65-358 of Table D.

In another aspect, the present invention provides a composition, comprising: a deuterium-enriched aldehyde selected from aldehydes 65-358 of Table E.

In another aspect, the present invention provides a composition, comprising: a deuterium-enriched aldehyde selected from aldehydes 65-358 of Table F.

In another aspect, the present invention provides a composition, comprising: a deuterium-enriched aldehyde selected from aldehydes 65-358 of Table G.

In another aspect, the present invention provides a composition, comprising: a deuterium-enriched aldehyde selected from aldehydes 65-358 of Table H.

In another aspect, the present invention provides a composition, comprising: a deuterium-enriched aldehyde selected from aldehydes 65-358 of Table I.

In another aspect, the present invention provides a composition, comprising: a deuterium-enriched aldehyde selected from aldehydes 65-358 of Table J.

In another aspect, the present invention provides a composition, comprising: a deuterium-enriched aldehyde selected from aldehydes 65-358 of Table K.

In another aspect, the present invention provides a composition, comprising: a deuterium-enriched aldehyde selected from aldehydes 65-358 of Table L.

Compounds of the present invention are more stable to autoxidation than the corresponding aldehydes where the hydrogen atom attached to the carbonyl moiety (i.e., H—C(O)) is not enriched in the deuterium isotope. For instance, where the deuterium isotope comprises greater than 90 percent of the subject hydrogen atoms, the rate of autoxidation—i.e., conversion of the aldehyde to its corresponding carboxylic acid through oxidation by atmospheric oxidation in the absence of an oxidation catalyst (e.g., metal or transition metal-based catalyst)—is reduced by at least 10 percent (e.g., if 10.0 percent of the aldehyde without deuterium enrichment experiences autoxidation, less than 9.0 percent of the aldehyde with deuterium enrichment experiences autoxidation under the same conditions). In certain cases, the rate is reduced by at least 20 percent, 30 percent, 40 percent, 50 percent, 60 percent, 70 percent, 80 percent or 90 percent.

Compounds 1-358 can be synthesized using any appropriate method. Examples of such methods include: reduction of the corresponding acid halide with deuterium gas (see U.S. Pat. No. 5,149,820); reduction of the corresponding tertiary amide using $Cp_2Zr(D)Cl$ (see Georg et al. *Tet. Lett.* 2004; 45: 2787-2789); and, reduction of the corresponding ester using $LiAlD_4$ to produce an alcohol and subsequent oxidation (see Kim et al., *J. Label Compd Radiopharm* 2004; 47: 921-934)(or just oxidation of a corresponding alcohol);

Alternatively, an additional method includes reduction of the un-enriched aldehyde with $NaBD_4$ or $NaCNBD_3$ followed by re-oxidation with pyridinium chlorochromate or another suitable oxidant, in which the deuterium enrichment of the aldehyde is a result of the isotope effect.

In another aspect, the present invention provides compositions comprising one or more of aldehydes 1-64 and an organic solvent (e.g., an alcohol (e.g., ethyl alcohol and isopropyl alcohol), ether (e.g., dimethyl ethyl), or alkane (e.g., hexanes)). In another aspect, the organic solvent is ethyl alcohol. Examples of the concentration of the ethyl alcohol include 50-97.5 weight percent, 60-97 weight percent, and 70-96 weight percent.

In another aspect, the present invention provides compositions comprising one or more of aldehydes 65-358 and an organic solvent (e.g., an alcohol (e.g., ethyl alcohol and isopropyl alcohol), ether (e.g., dimethyl ethyl), or alkane (e.g., hexanes)). In another aspect, the organic solvent is ethyl alcohol. Examples of the concentration of the ethyl alcohol include 50-97.5 weight percent, 60-97 weight percent, and 70-96 weight percent.

In another aspect, the compositions of the present invention comprise an additional ingredient. Examples of additional ingredients include: dipropylene glycol; isopropyl myristate; oils (e.g., coconut oil); and liquid waxes (e.g., jojoba oil).

The compositions discussed herein also can be used, for example, in a perfume. Reference to "perfume" means a mixture comprising fragrant compounds and solvents used to give the human body, animals, objects and living spaces a pleasant scent.

In another aspect, the present invention provides novel compositions for modulating the behavior of insects (e.g., attracting or inhibiting insect species), comprising: a deuterium-enriched aldehyde selected from structures 1-64, wherein the aldehyde is a pheromone and an optional additional component or components suitable for the composition (e.g., a pesticide, dispensing material or device, solvent, adhesive capable of trapping the insect, etc.).

In another aspect, the present invention provides novel compositions for modulating the behavior of insects (e.g., attracting or inhibiting insect species), comprising: a deuterium-enriched aldehyde selected from structures 65-358, wherein the aldehyde is a pheromone and an optional additional component or components suitable for the composition (e.g., a pesticide, dispensing material or device, solvent, adhesive capable of trapping the insect, etc.).

In another aspect, the composition comprises a pheromone blend.

A pheromone blend, comprises: at least one pheromone aldehyde selected from the deuterium-enriched aldehydes of the present invention and at least one additional pheromone that is either an un-enriched aldehyde or a different pheromone aldehyde selected from the deuterium-enriched aldehydes of the present invention.

In another aspect, the present invention provides novel methods for modulating the behavior of insects (e.g., attracting insect species or inhibiting the mating or aggregation of insect species), comprising:

a. applying a deuterium-enriched aldehyde pheromone of the present invention, or a composition comprising a deuterium-enriched aldehyde pheromone of the present invention and a optionally a solvent or other additional component suitable for the composition, to a surface of an object (e.g., a lure within a trap wherein the insect enters but cannot leave, a lure or trap wherein the insect sticks to a surface of the trap, or a lure or trap containing a chemical capable of killing the insect); and, b. placing the object in a location where one desires either to attract insect species or inhibiting the mating or aggregation of insect species.

In another aspect, a pheromone blend is applied (either neat or as a part of a composition of the present invention).

In another aspect, two or more deuterium-enriched aldehyde pheromones of the present invention are applied (either neat or as a part of a composition of the present invention).

Alternatively, the method comprises: distributing a composition comprising a deuterium-enriched aldehyde pheromone of the present invention into an area (e.g., by aerial spraying over crops), into a stored product (e.g., traps or disruptant dispensers in grain crops), onto vegetation (e.g., by manual application of dollops of an emulsion (e.g., SPLAT® type formulation) onto plants, vines, leaves, or shoots), or by applying by aerial dissemination or manual placement a composition of pheromone-impregnated chips, pheromone containing polymer hollow fibers, or pheromone containing rubber septa, in order to modulate the behavior of insects by disruption of mating behavior. More than one composition or method may be combined to achieve the desired reduction of crop damage.

In another aspect, a pheromone blend is present in the distributed composition.

In another aspect, two or more deuterium-enriched aldehyde pheromones of the present invention are present in the distributed composition.

In another aspect, the deuterium-enriched aldehyde pheromone of the present invention is distributed impregnated on a chip, in a polymer hollow fiber, or adsorbed within a rubber septum.

In another aspect, a pheromone blend is distributed impregnated on a chip, in a polymer hollow fiber, or adsorbed within a rubber septum.

In another aspect, two or more deuterium-enriched aldehyde pheromones of the present invention are distributed impregnated on a chip, in a polymer hollow fiber, or adsorbed within a rubber septum.

The modulation of insect behavior can comprise attraction to an aldehyde pheromone trap, or alternatively, disruption of mate-finding and mating behavior. A benefit of such insect behavior modulation can be diminished crop damage, such as reducing damage to fruits, nuts, seeds, grains, grapes, leaves, shoots, bark, grain, or other valuable crops by reducing insect damage to said crop, whether in the field or in storage after harvesting said valuable crop.

In another aspect, the modulating composition of the present invention, comprises: a deuterium-enriched aldehyde pheromone of the present invention formulated to be used in an attractant trap (an attractant composition).

In another aspect, the modulating composition of the present invention, comprises: a pheromone blend formulated to be used in an attractant trap (an attractant composition).

In another aspect, two or more deuterium-enriched aldehyde pheromones of the present invention are present in the modulating composition.

In another aspect, the present invention provides a method of using an attractant composition in an attractant trap.

In another aspect, the present invention provides a method of using a deuterium-enriched aldehyde pheromone as a component of a composition to attract, trap, or monitor adult insects in a stored product with the goal of minimizing crop product infestation and loss. In another aspect, a pheromone blend is in the composition. In another aspect, two or more deuterium-enriched aldehyde pheromones of the present invention are present in the composition.

In another aspect, the modulating composition of the present invention, comprises a deuterium-enriched aldehyde pheromone of the present invention formulated to be used as a mating disruptant (a disruptant composition). A disruptant composition is typically dispersed throughout part or all of an area to be protected.

In another aspect, a pheromone blend is present in the disruptant composition.

In another aspect, two or more deuterium-enriched aldehyde pheromones of the present invention are present in the disruptant composition.

In another aspect, the present invention provides a method of using a disruptant composition in an area to be protected (e.g., a crop field). It will be understood by those skilled in the art that disruption of mating by adult insects will reduce the population of offspring. Frequently it is the offspring, or larvae, of the species that are responsible for damage to the field crop or harvested crop product. A skilled person will understand that disruption of mating may be an indirect method of reducing damage to field crops or harvested crop products by larval forms of the insects that feed on the crop or crop product.

In another aspect, the disruptant composition is made using an oil/water emulsion preparation to deposit the disruptant onto a carrier. Examples of carriers include a polymeric hollow loop, a rubber (e.g., septum) or polymeric carrier, and impregnable chips.

Examples of types of attractant and/or disruptant formulations include: microencapsulation, hollow tube dispensers, bait stations, oil-water emulsions, and other volatile deuterium-enriched aldehyde dispensers.

Microencapsulation refers to encapsulating at least one deuterium-enriched aldehyde pheromone of the present invention in a polymer. The polymer is selected to delay the release of the pheromone for at least a few days. The microencapsulated pheromone(s) can be applied by spraying.

Examples of hollow tube dispensers include plastic twist-tie type dispensers, plastic hollow fibers, and plastic hollow microfibers. These types of dispensers are filled with at least one disruptant or a disruptant composition of the present invention and then distributed throughout the area to be protected.

Bait stations are stationary devices that are typically used to attract and kill Examples include platforms comprising at least pheromone aldehyde of the present invention and a glue board (or some other mechanism capable of trapping the attracted insect). Instead of or in addition to glue, the station can contain a pesticide that negatively affects the insect (e.g., reduces its ability to mate or reproduce).

Dispensers or high-emission dispensers are devices that either passively or actively release a pheromone aldehyde of the present invention. Examples of passive release include pheromone sachets or an emulsion (e.g., a SPLAT® (Specialized Lure And Pheromone Technology) formulation). Active dispensers may release bursts of at least one pheromone aldehyde of the present invention (or composition containing at least one pheromone aldehyde of the present invention) at timed intervals or by continuous release through volatilization from the dispenser.

As used herein, a pheromone is a deuterium-enriched aldehyde of structure 1 that has the traits of a natural pheromone, i.e., a chemical capable communicating with at least one insect species. Pheromones may act as alarm signals, provide trails to food sources, attract parasitoids or other predators, and/or attract insects of the same species for the purpose of mating.

Unless otherwise specified, when a pheromone is recited in the present invention it can be a single deuterium-enriched aldehyde of structure 1 or a blend of pheromones wherein at least one is a deuterium-enriched aldehyde of structure 1. The second, third, fourth, fifth, or more pheromone can be a deuterium-enriched aldehyde of structure 1 or a non-deuterium-enriched aldehyde In another aspect, a composition of the present invention, comprises: 2, 3, 4, 5, 6, 7, 8, 9, or 10 deuterium-enriched aldehyde pheromones of the present invention.

In another aspect, a composition of the present invention, comprises: 2 or more deuterium-enriched aldehyde pheromones of the present invention.

In another aspect, a composition of the present invention, comprises: 3 or more deuterium-enriched aldehyde pheromones of the present invention.

In another aspect, a composition of the present invention, comprises: 4 or more deuterium-enriched aldehyde pheromones of the present invention.

In another aspect, a composition of the present invention, comprises: 5 or more deuterium-enriched aldehyde pheromones of the present invention.

In another aspect, a composition of the present invention, comprises: at least 1, 2, 3, 4, or 5 deuterium-enriched aldehyde pheromones of the present invention and at least 1, 2, 3, 4, or 5 un-enrichedun-enriched pheromones.

In another aspect, a composition of the present invention, comprises: at least 1 deuterium-enriched aldehyde pheromone of the present invention and at least 1 un-enriched pheromone.

In another aspect, a composition of the present invention, comprises: at least 2 deuterium-enriched aldehyde pheromones of the present invention and at least 1 un-enriched pheromone.

In another aspect, a composition of the present invention, comprises: at least 1 deuterium-enriched aldehyde pheromones of the present invention and at least 2 un-enriched pheromones.

In another aspect, a composition of the present invention, comprises: at least 3 deuterium-enriched aldehyde pheromones of the present invention and at least 1 un-enriched pheromone.

In another aspect, a composition of the present invention, comprises: at least 3 deuterium-enriched aldehyde pheromones of the present invention and at least 2 un-enriched pheromones.

In another aspect, a composition of the present invention, comprises: at least 3 deuterium-enriched aldehyde pheromones of the present invention and at least 3 un-enriched pheromones.

Examples of insects for which a deuterium-enriched pheromone (or pheromones) can be prepared include: corn earworm (*Heliothis* (*Helicoverpa*) *zea*), tobacco budworm (*Heliothis virescens*), cotton bollworm (*Heliothis* (*Helicoverpa*) *armigera*), horse chestnut leaf miner (*Cameraria orhidella*), eastern spruce budworm (*Choristoneura fumiferana*), rice borer (*Chilo suppressalis*), grain weevils (*Trogoderma* spp.), grain/flower weevils (*Tribolium* spp.), cotton boll weevil (*Anthonomus grandis*), citrus leaf miner (*Phyllocnistis citrella*), carob moth (*Ectomyelois ceratoniae*), and Asian longhorn beetle (*Anoplophora glabripennis*), among many others. A complete listing of aldehyde pheromones of insects and the target species using the pheromones is available on the Pherobase.com data base and is hereby incorporated in totality into this application (http://www.pherobase.com/database/compound/compounds-aldes.php). One or more of the known aldehydic pheromones for these insects can be replaced by a deuterium-enriched aldehyde of the present invention.

For example, a pheromone composition for the corn earworm containing Z11-16:Ald can be replaced with compound 27 of the present invention. Representative examples of such deuterium-enriched aldehyde pheromones include compounds selected from: aldehydes 8, 15, 23, 24, 27, 28, 29, 30, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, and 64.

In another aspect, the present invention provides novel compositions for modulating the behavior of insects, comprising: at least one deuterium-enriched aldehyde that is a pheromone, wherein the deuterium-enriched aldehyde is selected from: aldehydes 27, 28, and 35.

In another aspect, the present invention provides novel compositions for modulating the behavior of insects, comprising: at least one deuterium-enriched aldehyde that is a pheromone, wherein the deuterium-enriched aldehyde is selected from: aldehydes 27 and 28.

In another aspect, the present invention provides novel compositions for modulating the behavior of insects, comprising: at least one deuterium-enriched aldehyde that is a pheromone, wherein the deuterium-enriched aldehyde is: aldehyde 36.

In another aspect, the present invention provides novel compositions for modulating the behavior of insects, comprising: at least one deuterium-enriched aldehyde that is a pheromone, wherein the deuterium-enriched aldehyde is selected from: aldehydes 37 and 38.

In another aspect, the present invention provides novel compositions for modulating the behavior of insects, comprising: at least one deuterium-enriched aldehyde that is a pheromone, wherein the deuterium-enriched aldehyde is selected from: aldehydes 27, 28, and 44.

In another aspect, the present invention provides novel compositions for modulating the behavior of insects, comprising: at least one deuterium-enriched aldehyde that is a pheromone, wherein the deuterium-enriched aldehyde is: aldehyde 49.

In another aspect, the present invention provides novel compositions for modulating the behavior of insects, comprising: at least one deuterium-enriched aldehyde that is a pheromone, wherein the deuterium-enriched aldehyde is: aldehyde 55.

In another aspect, the present invention provides novel compositions for modulating the behavior of insects, comprising: at least one deuterium-enriched aldehyde that is a pheromone, wherein the deuterium-enriched aldehyde is: aldehyde 59.

In another aspect, the present invention provides novel compositions for modulating the behavior of insects, comprising: at least one deuterium-enriched aldehyde that is a pheromone, wherein the deuterium-enriched aldehyde is selected from: aldehyde 40, 60, and 61.

In another aspect, the present invention provides novel compositions for modulating the behavior of insects, comprising: at least one deuterium-enriched aldehyde that is a pheromone, wherein the deuterium-enriched aldehyde is: aldehyde 62.

In another aspect, the present invention provides novel compositions for modulating the behavior of insects, comprising: at least one deuterium-enriched aldehyde that is a pheromone, wherein the deuterium-enriched aldehyde is: aldehyde 64.

Compounds of the present invention are also more stable to autoxidation than their corresponding non-deuterium enriched counterparts when included in compositions of the present invention. The rate of auto oxidation is reduced by at least 10 percent. In certain cases, the rate is reduced by at least 20 percent, 30 percent, 40 percent, 50 percent, 60 percent, 70 percent, 80 percent or 90 percent.

The skilled person will recognize that pheromones or pheromone blends for a given species may include non-aldehyde components, such as an alkyl, alkenyl, alkynyl alcohol or an alkyl, alkenyl or alkynyl ester. When the blend for optimal attraction includes such an additional non-aldehyde component, the skilled person would augment the deuterium-labeled pheromone of the present invention with the additional attractant or disruptant compound that increases the efficacy of modulation of the insect behavior, e.g., mating disruption or attraction to a trap.

In Table 1 are described examples of compositions of the present invention:

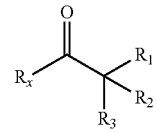

1 wherein:

there are at least $6\times10^{18}$ molecules of the aldehyde present in the composition;

$R_x$ is hydrogen, wherein the deuterium isotope is present in an amount greater than 0.10% of the $R_x$ hydrogen atoms;

unless otherwise defined, $R_1$, $R_2$ and $R_3$ are independently selected from hydrogen, alkyl, substituted alkyl, alkenyl, substituted alkenyl, alkynyl, substituted alkynyl, heteroalkyl, substituted heteroalkyl, aryl, substituted aryl, heteroaryl, and substituted heteroaryl;

alternatively, the $CR_1R_2R_3$ moiety forms a group selected from: an aryl, substituted aryl, heteroaryl, and substituted heteroaryl;

alternatively, the $CR_1R_2$ moiety forms a group a group selected from: an alkenyl and substituted alkenyl;

alternatively, the $CR_1R_2R_3$ moiety forms a group a group selected from: an alkynyl and substituted alkynyl; and, optionally, the aldehyde is substituted with $C(O)R_y$, wherein $R_x$ is hydrogen, wherein the deuterium isotope is present in an amount greater than 0.10% of the $R_y$ hydrogen atoms.

TABLE 1

| Ex. # | Structure # | $R_1$, $R_2$, $R_3$ | Solvent (weight %) |
|---|---|---|---|
| A. | 1 | As defined | Ethyl alcohol 70-96% by weight |
| B. | 1 | one of $R_1$, $R_2$ and $R_3$ is alkyl | Ethyl alcohol 70-96% by weight |
| C. | 1 | one of $R_1$, $R_2$ and $R_3$ is substituted alkyl | Ethyl alcohol 70-96% by weight |
| D. | 1 | one of $R_1$, $R_2$ and $R_3$ is alkenyl | Ethyl alcohol 70-96% by weight |
| E. | 1 | one of $R_1$, $R_2$ and $R_3$ is substituted alkenyl | Ethyl alcohol 70-96% by weight |
| F. | 1 | one of $R_1$, $R_2$ and $R_3$ is alkynyl | Ethyl alcohol 70-96% by weight |
| G. | 1 | one of $R_1$, $R_2$ and $R_3$ is substituted alkynyl | Ethyl alcohol 70-96% by weight |
| H. | 1 | one of $R_1$, $R_2$ and $R_3$ is heteroalkyl | Ethyl alcohol 70-96% by weight |

TABLE 1-continued

| Ex. # | Structure # | $R_1$, $R_2$, $R_3$ | Solvent (weight %) |
|---|---|---|---|
| I. | 1 | one of $R_1$, $R_2$ and $R_3$ is substituted heteroalkyl | Ethyl alcohol 70-96% by weight |
| J. | 1 | one of $R_1$, $R_2$ and $R_3$ is aryl | Ethyl alcohol 70-96% by weight |
| K. | 1 | one of $R_1$, $R_2$ and $R_3$ is substituted aryl | Ethyl alcohol 70-96% by weight |
| L. | 1 | one of $R_1$, $R_2$ and $R_3$ is heteroaryl | Ethyl alcohol 70-96% by weight |
| M. | 1 | one of $R_1$, $R_2$ and $R_3$ is substituted heteroaryl | Ethyl alcohol 70-96% by weight |
| N. | 1 | one of $R_1$, $R_2$ and $R_3$ is alkyl and another is hydrogen | Ethyl alcohol 70-96% by weight |
| O. | 1 | one of $R_1$, $R_2$ and $R_3$ is substituted alkyl and another is hydrogen | Ethyl alcohol 70-96% by weight |
| P. | 1 | one of $R_1$, $R_2$ and $R_3$ is alkenyl and another is hydrogen | Ethyl alcohol 70-96% by weight |
| Q. | 1 | one of $R_1$, $R_2$ and $R_3$ is substituted alkenyl and another is hydrogen | Ethyl alcohol 70-96% by weight |
| R. | 1 | one of $R_1$, $R_2$ and $R_3$ is alkynyl and another is hydrogen | Ethyl alcohol 70-96% by weight |
| S. | 1 | one of $R_1$, $R_2$ and $R_3$ is substituted alkynyl and another is hydrogen | Ethyl alcohol 70-96% by weight |
| T. | 1 | one of $R_1$, $R_2$ and $R_3$ is heteroalkyl and another is hydrogen | Ethyl alcohol 70-96% by weight |
| U. | 1 | one of $R_1$, $R_2$ and $R_3$ is substituted heteroalkyl and another is hydrogen | Ethyl alcohol 70-96% by weight |
| V. | 1 | one of $R_1$, $R_2$ and $R_3$ is aryl and another is hydrogen | Ethyl alcohol 70-96% by weight |
| W. | 1 | one of $R_1$, $R_2$ and $R_3$ is substituted aryl and another is hydrogen | Ethyl alcohol 70-96% by weight |
| X. | 1 | one of $R_1$, $R_2$ and $R_3$ is heteroaryl and another is hydrogen | Ethyl alcohol 70-96% by weight |
| Y. | 1 | one of $R_1$, $R_2$ and $R_3$ is substituted heteroaryl and another is hydrogen | Ethyl alcohol 70-96% by weight |
| Z. | 1 | $R_1$, $R_2$ and $R_3$ is alkyl and the other two are hydrogen | Ethyl alcohol 70-96% by weight |
| AA. | 1 | one of $R_1$, $R_2$ and $R_3$ is substituted alkyl and the other two are hydrogen | Ethyl alcohol 70-96% by weight |
| BB. | 1 | one of $R_1$, $R_2$ and $R_3$ is alkenyl and the other two are hydrogen | Ethyl alcohol 70-96% by weight |
| CC. | 1 | one of $R_1$, $R_2$ and $R_3$ is substituted alkenyl and the other two are hydrogen | Ethyl alcohol 70-96% by weight |
| DD. | 1 | one of $R_1$, $R_2$ and $R_3$ is alkynyl and the other two are hydrogen | Ethyl alcohol 70-96% by weight |
| EE. | 1 | one of $R_1$, $R_2$ and $R_3$ is substituted alkynyl and the other two are hydrogen | Ethyl alcohol 70-96% by weight |
| FF. | 1 | one of $R_1$, $R_2$ and $R_3$ is heteroalkyl and the other two are hydrogen | Ethyl alcohol 70-96% by weight |
| GG. | 1 | one of $R_1$, $R_2$ and $R_3$3 is substituted heteroalkyl and the other two are hydrogen | Ethyl alcohol 70-96% by weight |
| HH. | 1 | one of $R_1$, $R_2$ and $R_3$ is aryl and the other two hydrogen | Ethyl alcohol 70-96% by weight |
| II. | 1 | one of $R_1$, $R_2$ and $R_3$ is substituted aryl the other two are hydrogen | Ethyl alcohol 70-96% by weight |
| JJ. | 1 | one of $R_1$, $R_2$ and $R_3$ is heteroaryl and the other two are hydrogen | Ethyl alcohol 70-96% by weight |
| KK. | 1 | one of $R_1$, $R_2$ and $R_3$ is substituted heteroaryl and the other two are hydrogen | Ethyl alcohol 70-96% by weight |
| LL. | 1 | $CR_1R_2R_3$ is aryl | Ethyl alcohol 70-96% by weight |
| MM. | 1 | $CR_1R_2R_3$ is substituted aryl | Ethyl alcohol 70-96% by weight |
| NN. | 1 | $CR_1R_2R_3$ is heteroaryl | Ethyl alcohol 70-96% by weight |
| OO. | 1 | $CR_1R_2R_3$ is substituted heteroaryl | Ethyl alcohol 70-96% by weight |
| PP. | 1 | $CR_1R_2$ alkenyl and $R_3$ is hydrogen | Ethyl alcohol 70-96% by weight |
| QQ. | 1 | $CR_1R_2$ substituted alkenyl and $R_3$ is hydrogen | Ethyl alcohol 70-96% by weight |
| RR. | 1 | $CR_1R_2$ alkenyl and $R_3$ is alkyl | Ethyl alcohol 70-96% by weight |
| SS. | 1 | $CR_1R_2$ substituted alkenyl and $R_3$ is alkyl | Ethyl alcohol 70-96% by weight |
| TT. | 1 | $R_1$ is alkyl substituted with $C(O)R_y$. | Ethyl alcohol 70-96% by weight |

TABLE 1-continued

| Ex. # | Structure # | $R_1$, $R_2$, $R_3$ | Solvent (weight %) |
|---|---|---|---|
| UU. | 1 | $R_1$ is alkyl substituted with $C(O)R_y$ and $R_2$ and $R_3$ are hydrogens | Ethyl alcohol 70-96% by weight |
| VV. | 1 | $CR_1R_2R_3$ is aryl substituted with $C(O)R_y$. | Ethyl alcohol 70-96% by weight |
| WW. | 1 | $CR_1R_2R_3$ is substituted aryl substituted with $C(O)R_y$. | Ethyl alcohol 70-96% by weight |
| XX. | 2 | — | Ethyl alcohol 70-96% by weight |
| YY. | 3 | — | Ethyl alcohol 70-96% by weight |
| ZZ. | 4 | — | Ethyl alcohol 70-96% by weight |
| AAA. | 5 | — | Ethyl alcohol 70-96% by weight |
| BBB. | 6 | — | Ethyl alcohol 70-96% by weight |
| CCC. | 7 | — | Ethyl alcohol 70-96% by weight |
| DDD. | 8 | — | Ethyl alcohol 70-96% by weight |
| EEE. | 9 | — | Ethyl alcohol 70-96% by weight |
| FFF. | 10 | — | Ethyl alcohol 70-96% by weight |
| GGG. | 11 | — | Ethyl alcohol 70-96% by weight |
| HHH. | 12 | — | Ethyl alcohol 70-96% by weight |
| III. | 13 | — | Ethyl alcohol 70-96% by weight |
| JJJ. | 14 | — | Ethyl alcohol 70-96% by weight |
| KKK. | 15 | — | Ethyl alcohol 70-96% by weight |
| LLL. | 16 | — | Ethyl alcohol 70-96% by weight |
| MMM. | 17 | — | Ethyl alcohol 70-96% by weight |
| NNN. | 18 | — | Ethyl alcohol 70-96% by weight |
| OOO. | 19 | — | Ethyl alcohol 70-96% by weight |
| PPP. | 20 | — | Ethyl alcohol 70-96% by weight |
| QQQ. | 21 | — | Ethyl alcohol 70-96% by weight |
| RRR. | 22 | — | Ethyl alcohol 70-96% by weight |
| SSS. | 23 | — | Ethyl alcohol 70-96% by weight |
| TTT. | 24 | — | Ethyl alcohol 70-96% by weight |
| UUU. | 25 | — | Ethyl alcohol 70-96% by weight |
| VVV. | 26 | — | Ethyl alcohol 70-96% by weight |
| WWW. | 27 | — | Ethyl alcohol 70-96% by weight |
| XXX. | 28 | — | Ethyl alcohol 70-96% by weight |
| YYY. | 29 | — | Ethyl alcohol 70-96% by weight |
| ZZZ. | 30 | — | Ethyl alcohol 70-96% by weight |
| AAAA. | 31 | — | Ethyl alcohol 70-96% by weight |
| BBBB. | 32 | — | Ethyl alcohol 70-96% by weight |
| CCCC. | 33 | — | Ethyl alcohol 70-96% by weight |
| DDDD. | 34 | — | Ethyl alcohol 70-96% by weight |
| EEEE. | 35 | — | Ethyl alcohol 70-96% by weight |
| FFFF. | 36 | — | Ethyl alcohol 70-96% by weight |

TABLE 1-continued

| Ex. # | Structure # | R₁, R₂, R₃ | Solvent (weight %) |
|---|---|---|---|
| GGGG. | 37 | — | Ethyl alcohol 70-96% by weight |
| HHHH. | 38 | — | Ethyl alcohol 70-96% by weight |
| IIII | 39 | — | Ethyl alcohol 70-96% by weight |
| JJJJ. | 40 | — | Ethyl alcohol 70-96% by weight |
| KKKK. | 41 | — | Ethyl alcohol 70-96% by weight |
| LLLL. | 42 | — | Ethyl alcohol 70-96% by weight |
| MMMM. | 43 | — | Ethyl alcohol 70-96% by weight |
| NNNN. | 44 | — | Ethyl alcohol 70-96% by weight |
| OOOO. | 45 | — | Ethyl alcohol 70-96% by weight |
| PPPP. | 46 | — | Ethyl alcohol 70-96% by weight |
| QQQQ. | 47 | — | Ethyl alcohol 70-96% by weight |
| RRRR. | 48 | — | Ethyl alcohol 70-96% by weight |
| SSSS. | 49 | — | Ethyl alcohol 70-96% by weight |
| TTTT. | 50 | — | Ethyl alcohol 70-96% by weight |
| UUUU. | 51 | — | Ethyl alcohol 70-96% by weight |
| VVVV. | 52 | — | Ethyl alcohol 70-96% by weight |
| WWWW. | 53 | — | Ethyl alcohol 70-96% by weight |
| XXXX. | 54 | — | Ethyl alcohol 70-96% by weight |
| YYYY. | 55 | — | Ethyl alcohol 70-96% by weight |
| ZZZZ. | 56 | — | Ethyl alcohol 70-96% by weight |
| AAAAA. | 57 | — | Ethyl alcohol 70-96% by weight |
| BBBBB. | 58 | — | Ethyl alcohol 70-96% by weight |
| CCCCC. | 59 | — | Ethyl alcohol 70-96% by weight |
| DDDDD. | 60 | — | Ethyl alcohol 70-96% by weight |
| EEEEE. | 61 | — | Ethyl alcohol 70-96% by weight |
| FFFFF. | 62 | — | Ethyl alcohol 70-96% by weight |
| GGGGG. | 63 | — | Ethyl alcohol 70-96% by weight |
| HHHHH. | 64 | — | Ethyl alcohol 70-96% by weight |

Table 2: Examples A-HHHHH of Table 2 correspond to examples A-HHHHH of Table 1, except that the deuterium isotope in $R_x$ is in an amount greater than 2% of the hydrogen atoms present in $R_x$.

Table 3: Examples A-HHHHH of Table 2 correspond to examples A-HHHHH of Table 1, except that the deuterium isotope in $R_x$ is in an amount greater than 10% of the hydrogen atoms present in $R_x$.

Table 4: Examples A-HHHHH of Table 2 correspond to examples A-HHHHH of Table 1, except that the deuterium isotope in $R_x$ is in an amount greater than 50% of the hydrogen atoms present in $R_x$.

Table 5: Examples A-HHHHH of Table 2 correspond to examples A-HHHHH of Table 1, except that the deuterium isotope in $R_x$ is in an amount greater than 90% of the hydrogen atoms present in $R_x$.

In another aspect, compounds according to the present invention can be used to make resins and/or polymers. The method comprises the steps of: mixing a deuterium-enriched aldehyde selected from structures 1-64 with an aromatic compound (i.e., aryl-containing compound) or an olefinic compound (i.e., alkenyl-containing compound) in a solvent and in the presence of a catalyst, in such a way as to initiate a reaction between the aromatic or olefinic compound and the aldehyde; and, isolating the reaction product (e.g., resin or polymer) resulting from the reaction. The catalyst may be a Bronsted acid (e.g., aqueous sulfuric or hydrochloric acid), a Lewis acid (e.g., $AlCl_3$), a base (e.g., KOH) or a metal (e.g., transition metal). The reaction may be carried out at room temperature or at elevated temperature (e.g., 50° C., 60° C., 70° C., 80° C., 90° C., 100° C., 110° C. or 120° C.).

The reaction may also be carried out at atmospheric pressure or at elevated pressure (e.g., 2 atm, 3 atm, 4 atm or 5 atm).

In another aspect, compounds according to the present invention can be used to make resins and/or polymers. The method comprises the steps of: mixing a deuterium-enriched aldehyde selected from structures 65-358 with an aromatic compound (i.e., aryl-containing compound) or an olefinic compound (i.e., alkenyl-containing compound) in a solvent and in the presence of a catalyst, in such a way as to initiate a reaction between the aromatic or olefinic compound and the aldehyde; and, isolating the reaction product (e.g., resin or polymer) resulting from the reaction. The catalyst may be a Bronsted acid (e.g., aqueous sulfuric or hydrochloric acid), a Lewis acid (e.g., $AlCl_3$), a base (e.g., KOH) or a metal (e.g., transition metal). The reaction may be carried out at room temperature or at elevated temperature (e.g., 50° C., 60° C., 70° C., 80° C., 90° C., 100° C., 110° C. or 120° C.). The reaction may also be carried out at atmospheric pressure or at elevated pressure (e.g., 2 atm, 3 atm, 4 atm or 5 atm).

The rate of autoxidation of aldehydes in the polymerization/resin producing reaction is reduced by at least 10 percent as compared to use of non-deuterium enriched aldehydes under the same conditions. In certain cases, the rate is reduced by at least 20 percent, 30 percent, 40 percent, 50 percent, 60 percent, 70 percent, 80 percent or 90 percent.

The following general methods of making a resin and/or polymer are meant to illustrate, not limit, the present invention.

General Method 1

An aromatic compound (e.g., naphthalene, benzene, substituted benzene such as toluene) is heated in an acidic mixture (e.g., sulfuric acid and water) for 6 hours at 160° C. The mixture is cooled to 100° C., and a deuterium-enriched aldehyde selected from structures 1-64 is added in an amount that is less than a molar equivalent of the aromatic compound. The resulting mixture is kept at 100° C. at a time period ranging from 30 minutes to 16 hours to afford a condensation polymer.

General Method 1A

An aromatic compound (e.g., naphthalene, benzene, substituted benzene such as toluene) is heated in an acidic mixture (e.g., sulfuric acid and water) for 6 hours at 160° C. The mixture is cooled to 100° C., and a deuterium-enriched aldehyde selected from structures 65-358 is added in an amount that is less than a molar equivalent of the aromatic compound. The resulting mixture is kept at 100° C. at a time period ranging from 30 minutes to 16 hours to afford a condensation polymer.

General Method 2

To a mixture of a deuterium-enriched aldehydes selected from structures 1-64 and an aromatic alcohol (e.g., resorcinol) at room temperature is added an acidic solution (e.g., aqueous HCl). This affords a condensation polymer upon isolation.

General Method 2B

To a mixture of a deuterium-enriched aldehydes selected from structures 65-358 and an aromatic alcohol (e.g., resorcinol) at room temperature is added an acidic solution (e.g., aqueous HCl). This affords a condensation polymer upon isolation.

General Method 3

To an aromatic alcohol (e.g., phenol, resorcinol) in an organic solvent (e.g., ether such as dioxane) is slowly added acid (e.g., sulfuric acid). A deuterium-enriched aldehyde selected from structures 1-64 is added dropwise with stirring. The reaction mixture is heated and the contents refluxed for 2 hours. The organic solvent and water are removed, and the reaction mixture is cooled. Precipitation of material provides the condensation polymer.

General Method 3A

To an aromatic alcohol (e.g., phenol, resorcinol) in an organic solvent (e.g., ether such as dioxane) is slowly added acid (e.g., sulfuric acid). A deuterium-enriched aldehyde selected from structures 65-358 is added dropwise with stirring. The reaction mixture is heated and the contents refluxed for 2 hours. The organic solvent and water are removed, and the reaction mixture is cooled. Precipitation of material provides the condensation polymer.

General Procedure for Measurement of Aldehyde Oxidations

To a 12 mL clear, colorless, glass vial, fitted with a stir bar, was added the aldehyde (1 mmol), triacetin (2.0 mL), and water (0.10 mL, purified by reverse osmosis). The top of the vial was covered with a tissue and the mixture was stirred vigorously at room temperature. In the benzaldehyde reactions, (both H and D), 4.0 µL aliquots were withdrawn at 0, 0.5, 18, 25, 96, and 120 hour time points. These were diluted with ethanol (1.0 mL), and analyzed by HPLC. In the hexanal reactions (both H and D), 45 µL aliquots were withdrawn at 2, 4, 6, and 24 hour time points. These were diluted with ethanol (1.0 mL) and analyzed by GC.

Instruments and Conditions Used for Analysis:

High pressure liquid chromatography: Agilent XDB C18 50×4.6 mm 1.8 micron column Solvent A—Water (0.1% TFA)

Solvent B—Acetonitrile (0.07% TFA)

Gradient—5 min 95% A to 95% B then 1 minute hold. 1.5 mL/min

UV Detection (integration) @ 210 and 254 nm

Gas Chromatography:

HP 6890GC Column=Agilent DB-5 15 m×0.25 mm capillary column.

35° C. start (2 min hold), ramping to 100° C. at 5° C. per minute 7.8 mL/min gas flow Flame Ion Detection (Integration)

Example 1

The oxidation rate of deuterium enriched benzaldehyde (i.e., >95% deuterium at the α-H, i.e., H—C(O)Ph, "benzaldehyde-D") to benzoic acid was compared against un-enriched benzaldehyde (i.e., naturally occurring isotopic abundance, "benzaldehyde-H"), using the above-described procedure. The time and amount of aldehyde remaining were plotted as shown in FIG. 4. After 24 hours, approximately 90% of benzaldehyde-D remained (a 10% loss). In contrast, after 24 hours, approximately 30% of benzaldehyde-H remained (a 70% loss). The autoxidation of deuterium enriched benzaldehyde was reduced by over 50 percent after a period of approximately 24 hours due to the presence of deuterium.

Example 2

The oxidation rate of deuterium enriched hexanal (i.e., >95% deuterium at α-hydrogen i.e., H—$C(O)C_5H_{11}$, "hexanal-D") to hexanoic acid was compared against un-enriched hexanal (i.e., naturally occurring isotopic abundance, "hexanal-H") using the above-described procedure. The time and amount of aldehyde remaining were plotted as shown in FIG. 5. After 24 hours, approximately 90% of hexanal-D remained (a 10% loss). In contrast, after 24 hours, approximately 30% of hexanal-H remained (a 70% loss).

The autoxidation of deuterium-enriched hexanal was reduced by about 50 percent after a period of approximately 24 hours.

Numerous modifications and variations of the present invention are possible in light of the above teachings. It is therefore to be understood that within the scope of the appended claims, the invention may be practiced otherwise that as specifically described herein.

What is claimed is:

1. An insect behavior modulating composition for modulating the behavior of the citrus leafminer, *Phyllocnistis citrella*, comprising:
   (a) a deuterium-enriched aldehyde; and,
   (b) at least one of an additional component selected from: pesticide, solvent, and an adhesive capable of trapping the insect;
   wherein the deuterium-enriched aldehyde is of formula 61:

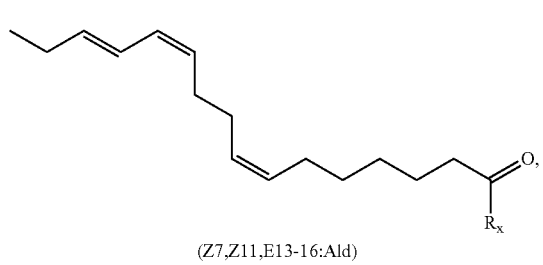

(Z7,Z11,E13-16:Ald)

wherein:
there are at least $6 \times 10^{18}$ molecules of the aldehyde in the composition;
$R_x$ is hydrogen, wherein the deuterium isotope is present in an amount greater than 0.10% of the $R_x$ hydrogen atoms.

2. The composition of claim 1, wherein the composition is sprayable.

3. The composition of claim 1, wherein the composition is an emulsion.

4. The composition of claim 1, wherein the deuterium-enriched aldehyde is microencapsulated.

5. The composition of claim 1, further comprising: a deuterium-enriched aldehyde of formula 60:

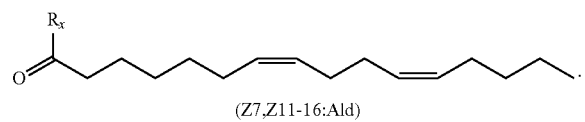

(Z7,Z11-16:Ald)

6. A method of modulating the behavior of the citrus leafminer, *Phyllocnistis citrella*, comprising:
   introducing a modulating composition to a field, wherein:
   the field, comprises: crops to be protected from the citrus leaf miner;
   the modulating composition, comprises: a composition of claim 1.

7. The method of claim 6, wherein the composition, further comprises: a deuterium-enriched aldehyde of formula 60:

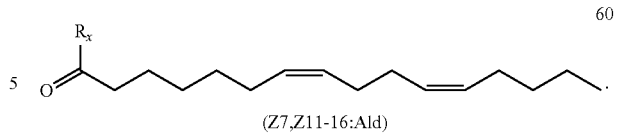

(Z7,Z11-16:Ald)

8. The method of claim 3, further comprising: harvesting the crops.

9. An insect behavior modulating composition for modulating the behavior of the cotton bollworm, *Helicoverpa armigera*, comprising:
   (a) a deuterium-enriched aldehyde; and,
   (b) at least one of an additional component selected from: pesticide, solvent, and an adhesive capable of trapping the insect;
   wherein the deuterium-enriched aldehyde is of formula 27:

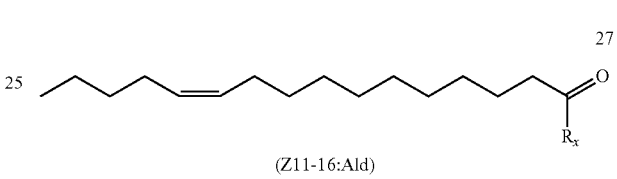

(Z11-16:Ald)

wherein:
there are at least $6 \times 10^{18}$ molecules of the aldehyde in the composition;
$R_x$ is hydrogen, wherein the deuterium isotope is present in an amount greater than 0.10% of the $R_x$ hydrogen atoms.

10. The composition of claim 9, wherein the composition, further comprises: a deuterium-enriched aldehyde of formula 28:

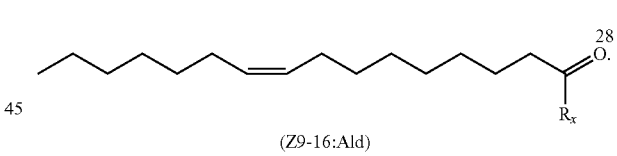

(Z9-16:Ald)

11. The composition of claim 9, wherein the composition is sprayable.

12. The composition of claim 9, wherein the composition is an emulsion.

13. The composition of claim 9, wherein the deuterium-enriched aldehyde is microencapsulated.

14. A method of modulating the behavior of the cotton bollworm, *Helicoverpa armigera*, comprising:
   introducing a modulating composition to a field, wherein:
   the field, comprises: crops to be protected from *H. armigera*;
   the modulating composition, comprises: a composition of claim 9.

15. The method of claim 14, wherein the composition, further comprises: a deuterium-enriched aldehyde of formula 28:

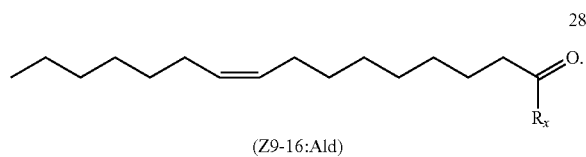

(Z9-16:Ald)

16. The method of claim 14, further comprising: harvesting the crops.

17. An insect behavior modulating composition, comprising:
(a) a deuterium-enriched aldehyde; and,
(b) at least one of an additional component selected from: pesticide, solvent, and an adhesive capable of trapping the insect;
wherein the deuterium-enriched aldehyde is of formula 315:

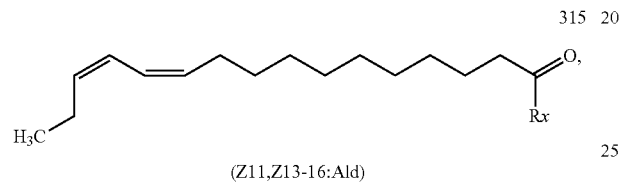

(Z11,Z13-16:Ald)

wherein:
there are at least $6 \times 10^{18}$ molecules of the aldehyde in the composition;
$R_x$ is hydrogen, wherein the deuterium isotope is present in an amount greater than 0.10% of the $R_x$ hydrogen atoms.

18. The composition of claim 17, wherein the composition is sprayable.

19. The composition of claim 17, wherein the composition is an emulsion.

20. The composition of claim 17, wherein the deuterium-enriched aldehyde is microencapsulated.

21. A method of modulating the behavior of insects, comprising:
introducing a modulating composition to a field, comprising:
crops to be protected from insects;
the modulating composition, comprising: a composition of claim 17.

22. The method of claim 21, further comprising: harvesting the crops.

* * * * *